US010973971B2

(12) United States Patent
Hinds et al.

(10) Patent No.: US 10,973,971 B2
(45) Date of Patent: *Apr. 13, 2021

(54) APPARATUS AND METHOD FOR UREA PHOTO-OXIDATION

(71) Applicant: University of Washington, Seattle, WA (US)

(72) Inventors: Bruce Hinds, Seattle, WA (US); Guozheng Shao, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/536,275

(22) Filed: Aug. 8, 2019

(65) Prior Publication Data
US 2020/0054810 A1 Feb. 20, 2020

Related U.S. Application Data

(63) Continuation of application No. PCT/US2019/044285, filed on Jul. 31, 2019.

(60) Provisional application No. 62/719,549, filed on Aug. 17, 2018.

(51) Int. Cl.
| | | |
|---|---|---|
| *A61M 1/16* | (2006.01) | |
| *A61M 1/34* | (2006.01) | |
| *A61M 1/36* | (2006.01) | |
| *A61M 1/28* | (2006.01) | |

(52) U.S. Cl.
CPC ........ *A61M 1/1696* (2013.01); *A61M 1/3406* (2014.02); *A61M 1/3472* (2013.01); *A61M 1/287* (2013.01); *A61M 1/3679* (2013.01); *A61M 2202/0057* (2013.01); *A61M 2202/0498* (2013.01)

(58) Field of Classification Search
None
See application file for complete search history.

(56) References Cited

U.S. PATENT DOCUMENTS

| | | | |
|---|---|---|---|
| 4,083,777 A | 4/1978 | Hutchisson | |
| 4,180,460 A | 12/1979 | Calari | |
| 5,247,434 A | 9/1993 | Peterson et al. | |
| 5,951,863 A * | 9/1999 | Kruger | A61M 1/28 210/134 |
| 8,597,505 B2 | 12/2013 | Fulkerson et al. | |

(Continued)

FOREIGN PATENT DOCUMENTS

| | | |
|---|---|---|
| CN | 104870372 A | 8/2015 |
| CN | 205598921 U | 9/2016 |

(Continued)

OTHER PUBLICATIONS

"Machine Translation of CN 104870372", Jin et al., published 2015, 29 total pages. (Year: 2015).*

(Continued)

*Primary Examiner* — Jonathan M Peo
(74) *Attorney, Agent, or Firm* — Christensen O'Connor Johnson Kindness PLLC

(57) ABSTRACT

Apparatus and method for photo-chemical oxidation are disclosed herein. In one embodiment, a dialysis fluid regeneration system includes: a nanostructured anode; a source of light configured to illuminate the anode; and a cathode that is oxygen permeable.

28 Claims, 20 Drawing Sheets

(56) References Cited

U.S. PATENT DOCUMENTS

| | | | |
|---|---|---|---|
| 8,834,696 | B2 | 9/2014 | Kim et al. |
| 2003/0217928 | A1 | 11/2003 | Lin et al. |
| 2005/0150832 | A1 | 7/2005 | Tsukamoto |
| 2010/0022937 | A1 | 1/2010 | Bedingfield et al. |
| 2010/0114012 | A1 | 5/2010 | Sandford et al. |
| 2011/0198225 | A1* | 8/2011 | Kim ............... B01D 57/02 204/452 |
| 2011/0315611 | A1 | 12/2011 | Fulkerson et al. |
| 2014/0138294 | A1* | 5/2014 | Fulkerson ......... A61M 1/3626 210/90 |
| 2014/0158986 | A1* | 6/2014 | Leung ............. B82Y 10/00 257/26 |
| 2014/0272183 | A1* | 9/2014 | Cooper ........... B01D 71/022 427/532 |
| 2014/0288351 | A1* | 9/2014 | Jones ............. A61N 5/06 600/9 |
| 2014/0346105 | A1 | 11/2014 | Tsukamoto |
| 2015/0209500 | A1 | 7/2015 | Lin et al. |
| 2016/0346839 | A1* | 12/2016 | Ishii ............. G06F 3/041 |
| 2017/0087291 | A1* | 3/2017 | Gerber ............ A61M 39/22 |
| 2017/0189594 | A1* | 7/2017 | Ding ............. C02F 1/4693 |
| 2017/0341942 | A1 | 11/2017 | Harper, Jr. |
| 2018/0065177 | A1 | 3/2018 | Ishii et al. |

FOREIGN PATENT DOCUMENTS

| | | |
|---|---|---|
| DE | 69732971 T2 | 2/2006 |
| EP | 0931581 A1 | 7/1999 |
| EP | 1374976 A1 | 1/2004 |
| EP | 1935441 A1 | 6/2008 |
| EP | 2862584 A1 | 4/2015 |
| JP | 2009160500 A | 7/2009 |
| KR | 10-2011-0033866 A | 3/2011 |
| KR | 10-2014-0024853 A | 3/2014 |
| KR | 20180089153 A | 8/2018 |
| NL | 8105027 A | 6/1983 |
| TW | 201529470 A | 8/2015 |
| WO | 2009/083011 A2 | 7/2009 |

OTHER PUBLICATIONS

Agar, J.W., "Understanding sorbent dialysis systems," Nephrology 2010; 15(4): 406-411.

Alizadeh, T., "Preparation of molecularly imprinted polymer containing selective cavities for urea molecule and its application for urea extraction," Analytica Chimica Acta 2010; 669(1-2): 94-101.

Salajka, J., et al., "High-affinity adsorption leads to molecularly ordered interfaces on TiO2 in air and solution," Science 2018; 361(6404): 786-789.

Bombelli, P. et al., "Quantitative analysis of the factors limiting solar power transduction by *Synechocystis* sp. PCC 6803 in biological photovoltaic devices," Energy & Environal Science 2011; 4(11): 4690-4698.

Cho, K., and Hoffmann, M.R., "Urea Degradation by Electrochemically Generated Reactive Chlorine Species: Products and Reaction Pathways," Environmental Science & Technology 2014; 48(19): 11504-11511.

Couser, W.G., et al., "The contribution of chronic kidney disease to the global burden of major noncommunicable diseases," Kidney International 2011; 80(12): 1258-1270.

Davenport, A., "Portable and wearable dialysis devices for the treatment of patients with end-stage kidney failure: Wishful thinking or just over the horizon?" Pediatr Nephrol 2015; 30(12): 2053-2060.

Davenport, A., et al., "A wearable haemodialysis device for patients with end-stage renal failure: a pilot study," The Lancet 2007; 370(9604): 2005-2010.

Duranton, F., et al., "Normal and pathologic concentrations of uremic toxins," Journal of the American Society of Nephrology 2012; 24(12): 1258-1270.

Eggers P.W., "Has the incidence of end-stage renal disease in the USA and other countries stabilized?" Current Opinion in Nephrology and Hypertension 2011; 20(3): 241-245.

Girishkumar, G., et al., "Lithium-Air Battery: Promise and Challenges," The Journal of Physical Chemistry Letters 2010; 1(14): 2193-2203.

Gordon, A., et al., "A Sorbent Based Low Volume Recirculating Dialysate System," Transactions of the American Society for Artificial Internal Organs 1969; 15: 347.

Hattori, A., and Tada, H., "High photocatalytic activity of F-doped TiO2 film on glass," Journal of Sol-Gel Science and Technology 2001; 22(1-2): 47-52.

Himmelfarb, J., and Ikizler, T.A., "Hemodialysis," The New England Journal of Medicine 2010; 363(19): 1833-1845.

Hinds, B., "Dramatic transport properties of carbon nanotube membranes for a robust protein channel mimetic platform," Current Opinion in Solid State and Materials Science 2012; 16(1): 1-9.

Hoang, S., et al., "Enhancing Visible Light Photo-oxidation of Water with TiO2 Nanowire Arrays via Cotreatment with H2 and NH3: Synergistic Effects between Ti3+ and N," Journal of the American Chemical Society 2012; 134(8): 3659-3662.

Huang, S.Y., et al., "Charge Recombination in Dye-Sensitized Nanocrystalline TiO2 Solar Cells," The Journal of Physical Chemistry B 1997; 101(14): 2576-2582.

Joshi, R.K., et al., "Precise and Ultrafast Molecular Sieving Through Graphene Oxide Membranes," Science 2014; 343(6172): 752-754.

Kaneko, M., et al., "Biophotochemical cell (BPCC) to photodecompose biomass and bio-related compounds by irradiation with simultaneous electrical power generation," Journal of Photochemistry and Photobiology A: Chemistry 2009; 205(2-3): 168-172.

Klarenbach, S.W., et al., "Economic evaluation of dialysis therapies," Nature Reviews Nephrology 2014; 10: 644-652.

Kooman, J.P., et al., "Creating a wearable artificial kidney: where are we now?" Expert Review of Medical Devices 2015; 12(4): 373-376.

Liu, B., and Aydil, E.S., "Growth of Oriented Single-Crystalline Rutile TiO2 Nanorods on Transparent Conducting Substrates for Dye-Sensitized Solar Cells," Journal of the American Chemical Society 2009; 131(11): 3985-3990.

Nijenhuis, W.F., et al., "Urea transport by macrocyclic carriers through a supported liquid membrane," Journal of the American Chemical Society 1991; 113(9): 3607-3608.

Park, S.-J., et al., "A versatile ultra-thin Au nanomesh from a reusable anodic aluminium oxide (AAO) membrane," Journal of Materials Chemistry C 2013; 1(34): 5330-5335.

Paudel, K.S., et al., "Programmable Transdermal Delivery of Nicotine in Hairless Guinea Pigs Using Carbon Nanotube Membrane Pumps," Journal of Pharmaceutical Sciences 2012; 101(10): 3823-3832.

Rinaldi, A., et al., "Engineering materials and biology to boost performance of microbial fuel cells: a critical review," Energy & Environmental Science 2008; 1: 417-429.

Shao, G., et al., "Intensity-Modulated Scanning Kelvin Probe Microscopy for Probing Recombination in Organic Photovoltaics," ACS Nano 2014; 8(10): 10799-10807.

Simka, W., et al., "Influence of anode material on electrochemical decomposition of urea," Electrochimica Acta 2007; 52(18): 5696-5703.

Smakman, R., and A.W.J. Vandoorn, "Urea Removal by Means of Direct Binding," Clinical Nephrology 1986; 26(6): S58-S62.

Stanca, S.E., et al., "Chemical and Electrochemical Synthesis of Platinum Black," Scientific Reports 2017; 7 (Article No. 1074: 8 pages.

Stephens, R.L., et al., "Portable-Wearable Artificial-Kidney (WAK)—Initial Evaluation," Kidney International 1975; 8: 123-132.

Topfer, L.-A., "Wearable Artificial Kidneys for End-Stage Kidney Disease," CADTH Issues in Emerging Health Technologies, Jan. 2017: 13 pages.

Urbanczyk, E., et al., "Urea removal from aqueous solutions—a review," Journal of Applied Electrochemistry 2016; 46(10): 1011-1029.

(56) References Cited

OTHER PUBLICATIONS

Wang, G.M., et al., "Solar driven hydrogen releasing from urea and human urine," Energy & Environmental Science 2012; 5(8): 8215-8219.
Wang, G., et al., "Hydrogen-Treated TiO2 Nanowire Arrays for Photoelectrochemical Water Splitting," Nano Letters 2011; 11(7), 3026-3033.
Wester, M., et al., "Removal of Urea in a Wearable Dialysis Device: A Reappraisal of Electro-Oxidation," Artificial Organs 2014; 38(12): 998-1006.
Xiao, J., et al., "Hierarchically Porous Graphene as a Lithium-Air Battery Electrode," Nano Letters 2011; 11(11): 5071-5078.
Yao, S.J., et al., "Anodic-Oxidation of Urea and an Electrochemical Approach to De-Ureation," Nature 1973; 241 (5390), 471-472.
Zhao, B.-X., et al., "Microstructure and optical properties of TiO2 thin films deposited at different oxygen flow rates," Transactions of Nonferrous Metals Society of China 2010; 20(8): 1429-1433.
Zhou, X., et al., "Self-assembling subnanometer pores with unusual mass-transport properties," Nature Communications 2012; 3 (Article No. 949): 8 pages.
Park, S., Lee, J.T. and Kim, J., "Photocatalytic oxidation of urea on TiO2 in water and urine: mechanism, product distribution, and effect of surface platinization," Environmental Science and Pollution Research, Jan. 2019, 26(2): 1044-1053.
Kaneko, M., Ueno, H., Saito, R., Suzuki, S., Nemoto, J., and Fujii, Y., "Biophotochemical cell (BPCC) to photodecompose biomass and bio-related compounds by UV irradiation with simultaneous electrical power generation," Journal of Photochemistry and Photobiology A: Chemistry, Jun. 2009, 205(2-3): 168-172.
International Search Report and Written Opinion, dated Nov. 5, 2019, issued in priority International Application No. PCT/US2019/044285, filed Jul. 31, 2019, 17 pages.

* cited by examiner

APPARATUS AND METHOD FOR UREA PHOTO-OXIDATION

CROSS-REFERENCE TO RELATED APPLICATION

This application is a continuation of International Application No. PCT/US2019/44285, filed Jul. 31, 2019, which claims the benefit of U.S. Provisional Application No. 62/719,549, filed Aug. 17, 2018; which applications are incorporated herein by reference in their entireties.

BACKGROUND

More than 2 million end-stage renal disease (ESRD) patients worldwide receive dialysis to sustain life, with this number likely to represent less than 10% of the actual need. In the United States alone, over 460,000 people are on kidney dialysis, over 89,000 of whom die annually with a 5-year survival rate being only 35%. The intermittent character of hemodialysis causes large fluctuations in blood metabolite concentrations. Observations show that long-term survival in dialysis is improved for the patients treated by extended hemodialysis (i.e., more frequent or with longer hours of treatment) when compared to conventional hemodialysis.

FIG. 1 is a plan view of a conventional dialysis system 10. In operation, a patient 5 is connected to the dialysis system 10 such that patient's blood flows through a tubing 14 into a dialysis system 10. The tubing 14 is threaded through a blood pump 18. The pumping action of the blood pump 18 pushes patient's blood through the dialysis system 10 and back into patient's body. The pump 18 is typically a non-contact pump.

Dialysate 12 is a fluid that helps remove the unwanted waste products (e.g., urea) from patient's blood. During the dialysis, dialysate 12 and patient's blood flow through the dialysis system 10, but the two flows do not physically mix. Instead, fresh dialysate 12 from the machine is separated by a membrane from the blood flow. Impurities from patient's blood stream are filtered out through the membrane into dialysate 12. For example, typically 12-24 g of urea needs to be removed daily in a normal adult, but with a reduced protein diet 15 g day is a sufficient goal. Other impurities are also filtered out of the blood stream into the dialysate. Dialysate containing unwanted waste products and excess electrolytes leave the dialyzer for disposal.

Since hemodialysis works on the principle of diffusion into a dialysate having low target concentration, inherently large volumes of fluid are required. The conventional hemodialysis achieves the removal of excessive metabolic waste from the body by running about 120 liters of dialysate per session, which typically requires 3-4 hours of treatment. The dialysis may be required three times a week. Patients are subjected to significant life disruptions, including having to be immobilized for hours and having to arrange transportation to dialysis centers, which impact their quality of life. Accordingly, systems and method for improved dialysis, including improved urea removal, are required.

SUMMARY

This summary is provided to introduce a selection of concepts in a simplified form that are further described below in the Detailed Description. This summary is not intended to identify key features of the claimed subject matter.

Briefly, the inventive technology is directed to urea removal from a dialysate. The inventive technology may be used for dialysis, including kidney dialysis, hemodialysis, hemofiltration, hemodiafiltration, removal of impurities, etc.

In some embodiments, a photo-chemical oxidation (also referred to as "dialysis-fluid regeneration" or "urea treatment") removes urea from dialysate. A dialysis system fluid regeneration system may include: a nanostructured anode; a source of light configured to illuminate the anode; and a cathode that is oxygen permeable. The nanostructures may be TiO2 nanowires that are hydrothermally grown. The source of light may be provided by an array of LEDs. The oxygen permeable or air permeable cathode may be a platinum-coated (Pt-coated) cloth or paper.

In some embodiments, the system may be sized down enough to become wearable and/or portable. Wearable dialysis devices not only achieve continuous dialysis, but also help reduce clinic related treatment costs and improve quality of life through enhanced mobility.

In one embodiment, a dialysis fluid regeneration system includes: a nanostructured anode; a source of light configured to illuminate the anode; and a cathode that is oxygen permeable.

In one aspect, the dialysis fluid is a dialysate. In another aspect, the system is a kidney dialysis system. In one aspect, the system is a hemofiltration system. In one aspect, the system is a hemodialysis system. In one aspect, the system is a hemodiafiltration system.

In one aspect, the system also includes a source of electrical voltage operationally coupled to the anode and the cathode. In another aspect, the source of electrical voltage is portable.

In one aspect, the dialysis fluid regeneration system is portable. In another aspect, the dialysis fluid regeneration system is wearable. In another aspect, the dialysis fluid regeneration system is stationary.

In one aspect, the anode, the source of light, and the cathode that is oxygen permeable are parts of a first dialysis-fluid regeneration cell, and the system includes a plurality of dialysis-fluid regeneration cells.

In one aspect, the cathode is an air-breathable cathode. In another aspect, the cathode is a conductive cloth-based cathode. In one aspect, the cloth is a platinum-coated (Pt-coated) cloth. In one aspect, the cathode is a conductive paper-based cathode.

In one aspect, the cathode is configured to electrochemically split water. In another aspect, the nanomaterial of the anode is configured to generate photo-electrons or holes when exposed to light.

In one aspect, the source of light comprises an array of light emitting diodes (LEDs). In one aspect, the LEDs are arranged in a two-dimensional (2D) array. In another aspect, the LEDs generate an irradiance of less than 4 mW/cm2 at a surface of the anode. In one aspect, the LEDs emit light at 365 nm wavelength.

In one aspect, the source of light comprises a source of UV. In another aspect, the source of light comprises a source of visible light. In one aspect, an incident photon to photo-electron efficiency is about 51%.

In one aspect, the nanostructured anode comprises $TiO_2$ nanowires. In another aspect, the individual nanowires have a thickness of about 500 nm. In one aspect, the $TiO_2$ nanowires are prepared hydrothermally. In one aspect, the nanowires are disposed on a substrate, and the individual nanowires are individually electrically coupled to a substrate that carries the nanowires.

In one aspect, a dialysate solution has a concentration of urea of 10 mM or less. In another aspect, the system also includes a radical scavenger configured to remove oxidative byproducts, radical byproducts, and chlorine.

In one aspect, the system also includes a membrane configured for passing small molecules through and for blocking large molecules from passing through. In another aspect, the membrane is a reverse osmosis (RO) membrane.

In one embodiment, a dialysis fluid regeneration system includes: a nanostructured substrate configured to generate photo-electrons or holes when exposed to light; a source of light configured to illuminate the substrate; and an oxygen permeable barrier.

In one aspect, the source of light is naturally occurring.

In one embodiment, a method for regenerating a dialysis fluid includes: flowing the dialysis fluid through a system of any of the preceding claims; and illuminating the anode with the source of light as the dialysis fluid passes over the anode, thereby photo-electrochemically eliminating urea in the dialysis fluid.

In one embodiment, a method for regenerating a dialysis fluid includes: flowing the dialysis fluid between an anode and a cathode of a dialysis system, wherein the anode comprises a plurality of nanostructures; illuminating the anode with a source of light; flowing oxygen through the cathode toward the dialysis fluid; and converting urea in the dialysis fluid into $CO_2$, $N_2$ and $H_2O$ thereby regenerating the dialysis fluid.

In one aspect, the method also includes recirculating the dialysis fluid within a dialysis system.

In one aspect, the method also includes: coupling a positive voltage to the anode; and coupling a negative voltage to the cathode.

In one aspect, the voltage differential between the positive voltage and the negative voltage is within a range from about 0.6 V to about 0.8 V.

In one aspect, the source of light includes a source of UV light and visible light.

In one aspect, flowing oxygen through the cathode toward the dialysis fluid includes flowing ambient air through the cathode.

In one aspect, the method also includes: flowing the dialysis fluid through a radical scavenger; and removing chlorine from the dialysis fluid in the radical scavenger.

In one embodiment, a method for preparing a dialysis fluid includes: flowing water to be treated between an anode and a cathode of a dialysis fluid regeneration system, wherein the anode comprises a plurality of nanostructures; illuminating the anode with a source of light; flowing oxygen through the cathode toward water to be treated; and oxidizing impurities in the water to be treated, thereby generating the dialysis fluid.

In one aspect, the method also includes recirculating the dialysis fluid within a dialysis system. In one aspect, the method also includes: coupling a positive voltage to the anode; and coupling a negative voltage to the cathode.

DESCRIPTION OF THE DRAWINGS

The foregoing aspects and many of the attendant advantages of the inventive technology will become more readily appreciated as the same are understood with reference to the following detailed description, when taken in conjunction with the accompanying drawings, wherein.

DETAILED DESCRIPTION

While several embodiments have been illustrated and described, it will be appreciated that various changes can be made therein without departing from the spirit and scope of the claimed subject matter.

Figure 1:
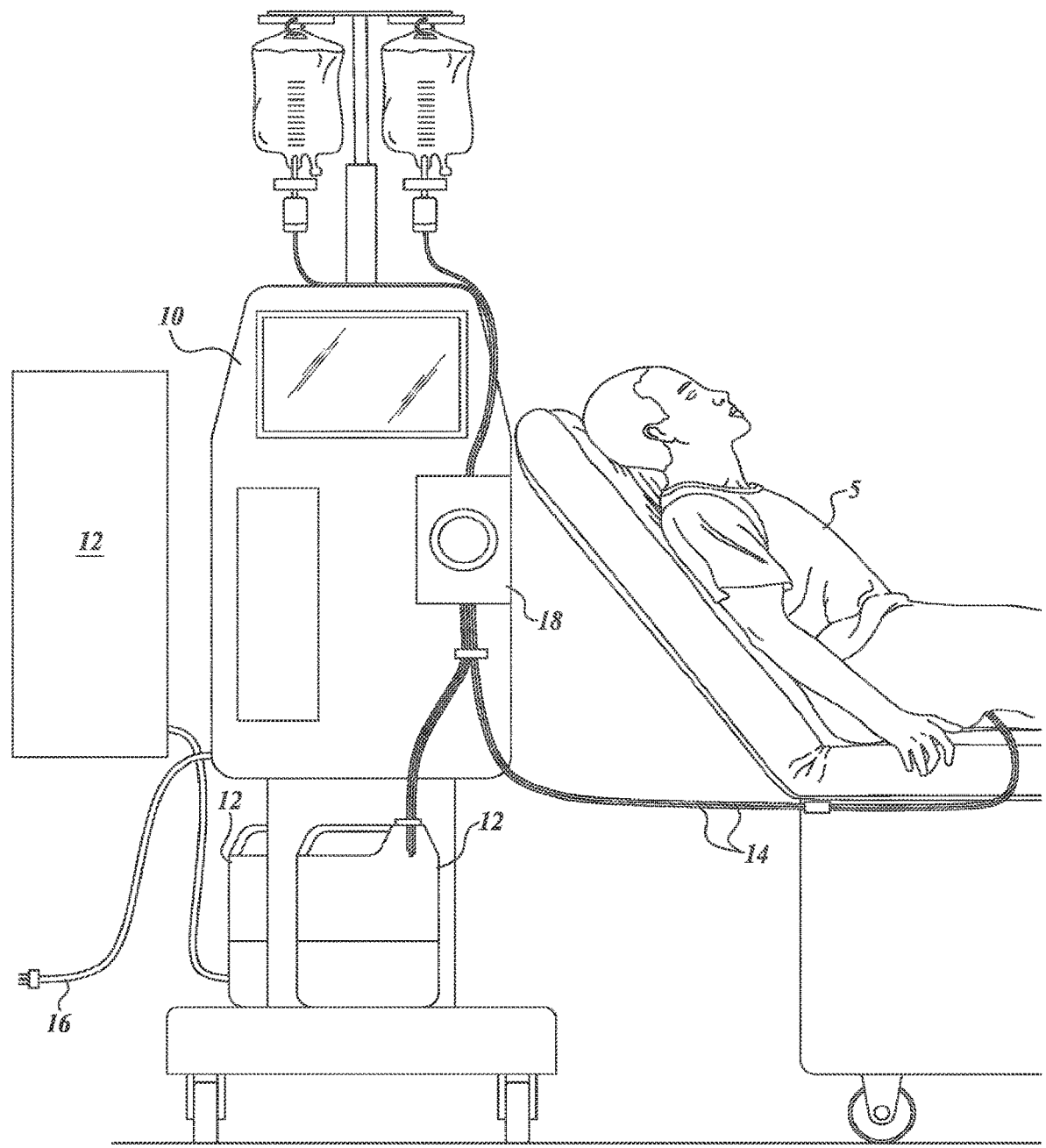
FIG. 1 is a plan view of a dialysis system in accordance with conventional technology.
Figure 2:
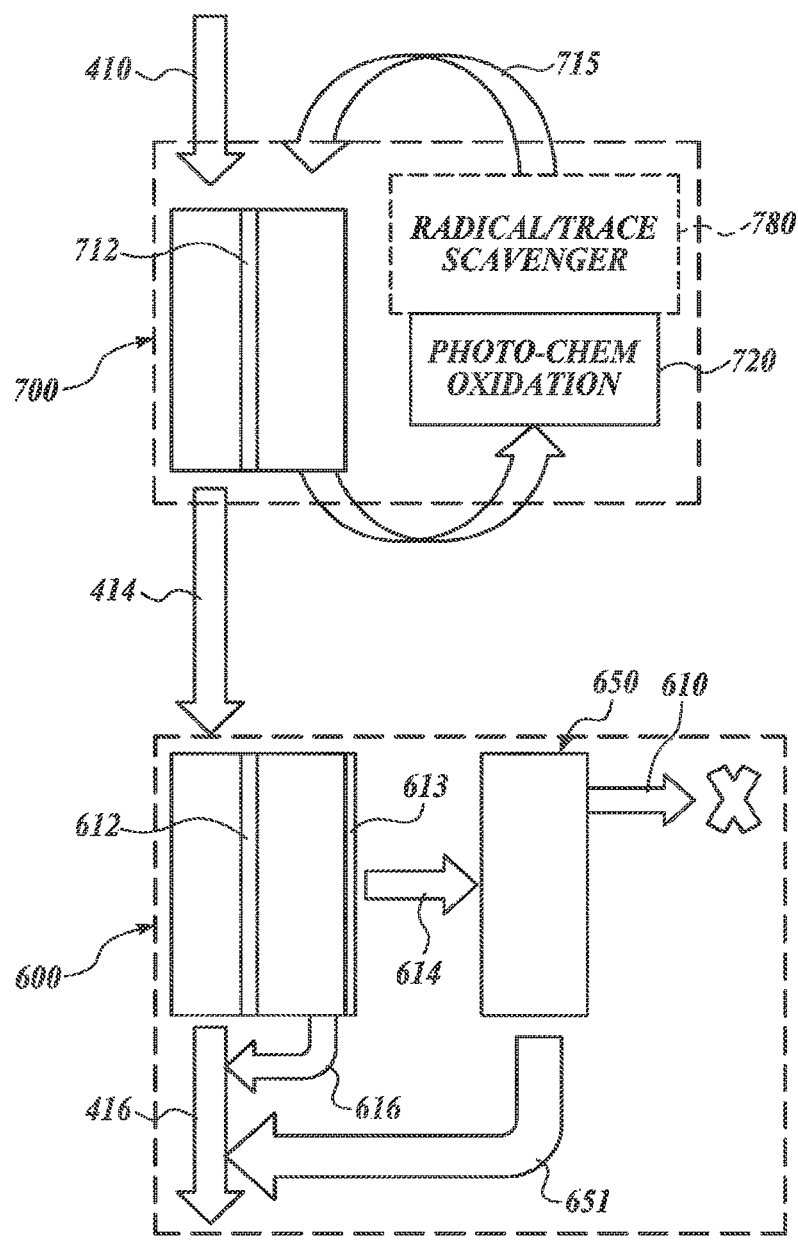
FIG. 2 is a schematic diagram of a dialysis system in accordance with an embodiment of the present technology.

FIG. 2 is a schematic diagram of a dialysis system in accordance with an embodiment of the present technology. The illustrated system (e.g., a kidney dialysis system, hemodialysis, hemodiafiltration or a hemofiltration system) includes a urea oxidation unit 700 and a toxin selective removal unit 600. In operation, flow of blood 410 that includes urea and other toxins enters the urea oxidation unit 700. The flow of blood 410 is separated from a flow of dialysate fluid (e.g., dialysate) 715 by a membrane 712, which allows mass exchange for select molecules between the flow of blood and the flow of dialysate fluid (referred to as "dialysate" for simplicity). In some embodiments, a low molecular weight cut-off dialysis membrane allows only small molecules (e.g., less than 100 Da) to pass through. In some embodiments, the membrane may be a reverse osmosis (RO) membrane. In some embodiments, the urea oxidation unit 700 includes a photo-chemical oxidation unit 720 (also referred to as a "dialysis-fluid regeneration unit", or a "urea treatment unit") that is configured to remove urea, and a radical/trace scavenger 780 that is configured to remove oxidative byproducts, radical byproducts, chlorine, and/or other toxins. The photo-chemical oxidation unit 720 is described in more detail with reference to FIGS. 4A to 8 below. Terms "photo-oxidation," "photochemical oxidation," and "photo-chemical oxidation" are used interchangeably in this specification.

In some embodiments, after urea and/or other small molecule toxins are removed from the blood flow 410, thus partially cleaned blood flow 414 continues to flow toward a protein-bound toxin selective removal unit 600. The blood flow 414 is separated from cellular components by a membrane 612 that is configured for passing large molecular weight proteins and small molecules, commonly referred to as blood plasma. On the permeate side of membrane 612 are selective sorbents for clearance of larger molecular weight and/or protein-bound toxins. This solution 614 flows through a membrane 613 into unit 650 with a mixture of sorbents and selective membranes for the removal of small molecule toxins through flow 610. Nutrients are returned to blood stream 416 as flow 651 as well as desorbed proteins in flow 616 on permeate/plasma side of membrane 612. Some non-exclusive examples of toxins 610 removed by the unit 600 are indoxyl sulfate that was bound to human albumin. Generally, the urea oxidation unit 700 removes small toxic molecules, while the toxin selective removal unit 600 removes large toxic molecules or those bound to proteins such as albumin. However, in different embodiments different arrangements of the toxin removal units are also possible. The blood and/or blood plasma flow 616 that exits from the toxin selective removal unit 600 continues to flow toward further elements/steps of the dialysis process or returns to the patient.

Figure 3:
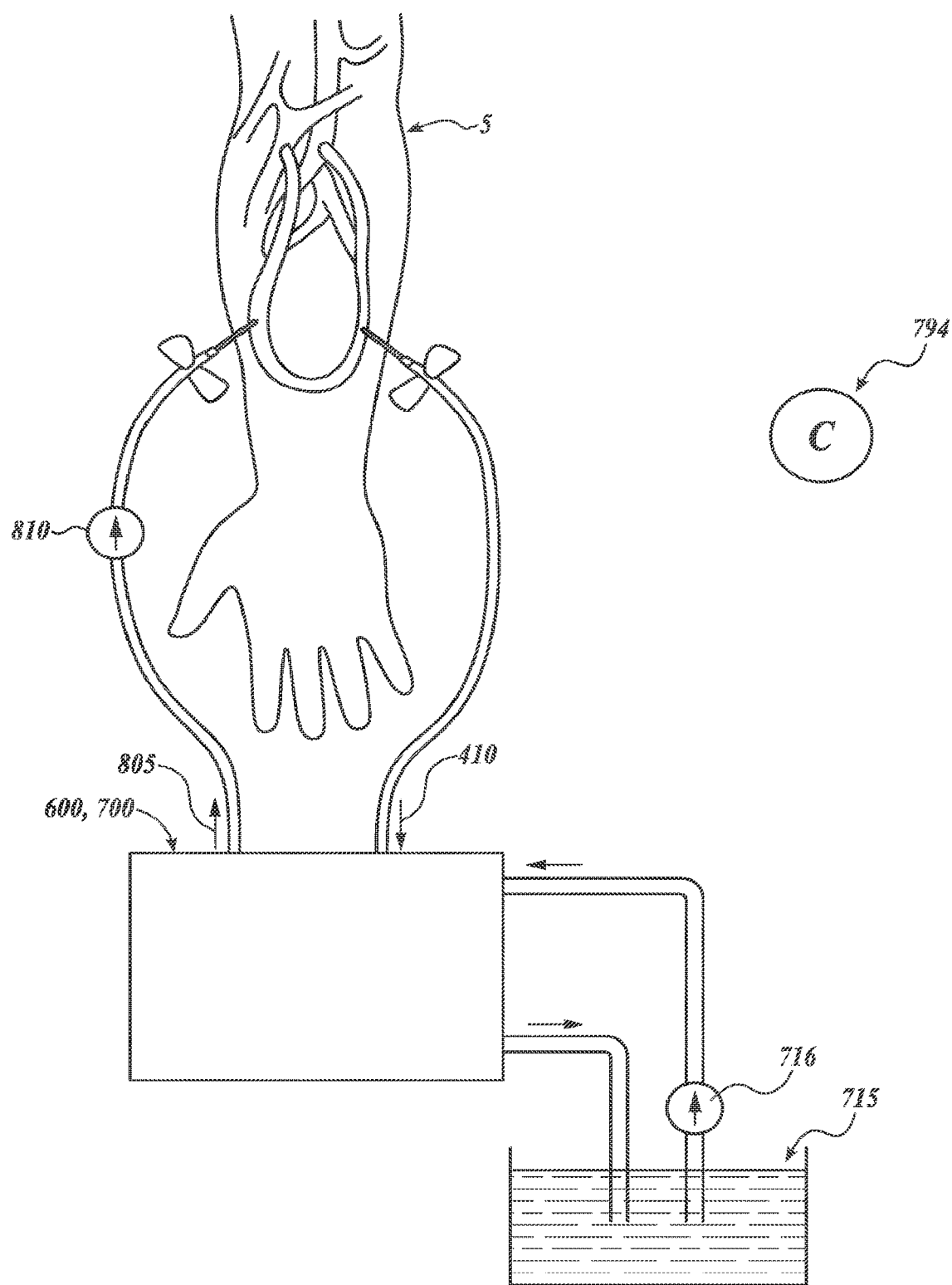
FIG. 3 is a schematic diagram of a dialysis system in operation in accordance with an embodiment of the present technology.

FIG. 3 is a schematic diagram of a dialysis system in operation in accordance with an embodiment of the present technology. The illustrated analysis system operates as a regeneration system for dialysate 715. In operation, blood flow 410, 805 flows between the vascular system of the patient, and the urea oxidation unit 700 and the toxin selective removal unit 600 (or other toxin removal units) generally requiring a pump (e.g., a pump 810). In some embodiments, the flow of dialysate 715 recirculates within the units 600, 700, therefore eliminating or at least limiting a need for adding fresh dialysate to the process. As a result, consumption of the dialysate is reduced with the embodiments of the inventive technology in comparison with the conventional dialysis.

The dialysate 715 may have a concentration of urea of 10 mM or less. In some embodiments, a controller 794 may control operation of pumps 810 and 716 to regulate the flow of blood input 410 and the dialysate 715.

Figure 4A:
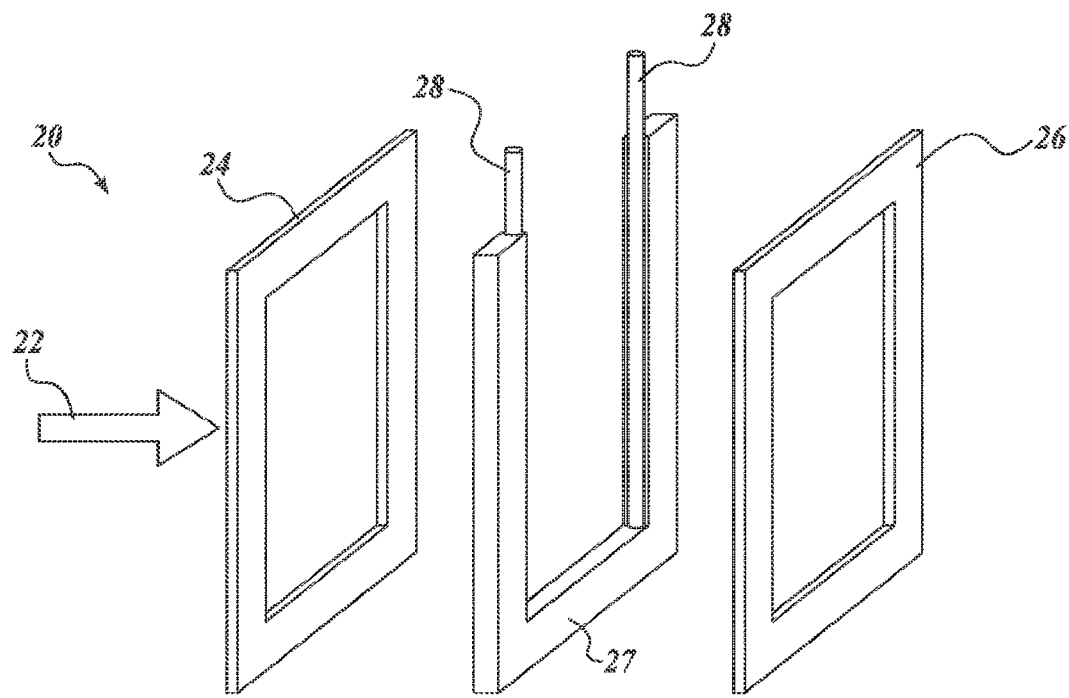
FIG. 4A is an exploded view of a urea treatment unit in accordance with an embodiment of the present technology.

FIG. 4A is an exploded view of a urea treatment unit 20 in accordance with an embodiment of the present technology. Illustrated urea treatment unit 20 is a photo-electric urea treatment unit that removes urea by an electrochemical reaction. The system 20 includes two electrodes 24, 26 that are separated by a dielectric spacer 27 (e.g., rubber, silicon, or plastic spacer). In operation, dialysate that contains urea is held between the two electrodes 24, 26, and is subjected to photo-illumination that promotes photo-oxidation of urea into $CO_2$, $H_2O$ and $N_2$.

The required source of light may be provided by an ultraviolet (UV) lamp 22. The reaction also requires oxygen for the electrochemical reaction. Providing required oxygen is described with reference to FIG. 4B below.

Figure 4B:
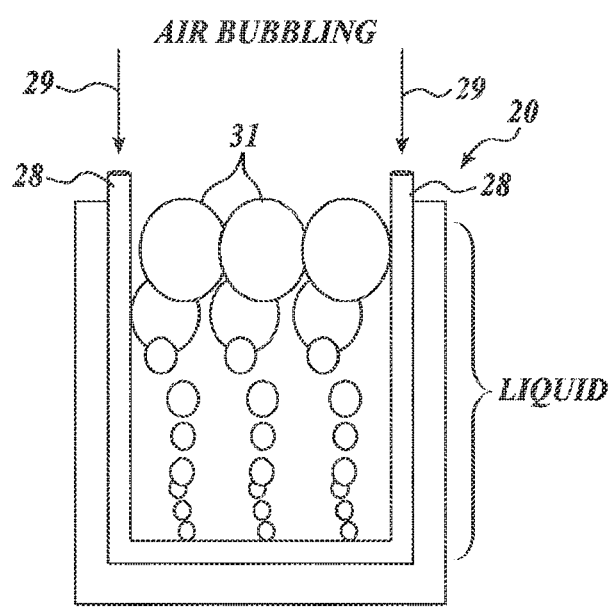
FIG. 4B is a schematic view of a urea treatment unit in operation in accordance with an embodiment of the present technology.

FIG. 4B is a schematic diagram of a urea treatment unit in operation in accordance with an embodiment of the present technology. In the illustrated embodiment, air flows into tubing 28 and further to the dialysate that contains urea inside the photo-electric urea treatment unit 20. Arrows 29 indicate the incoming flow of air that produces bubbles 31 in the dialysate. However, the quantum efficiency for incident photons from the UV lamp 22 to electrochemical reaction may be relatively low, sometimes less than 1%. As a result, the urea treatment unit 22 may still be impractically large if the target of about 15 to 20 g of urea removal is to be achieved in a portable device. Improved provisioning of oxygen is described with respect to FIG. 5A below.

Figure 5A:
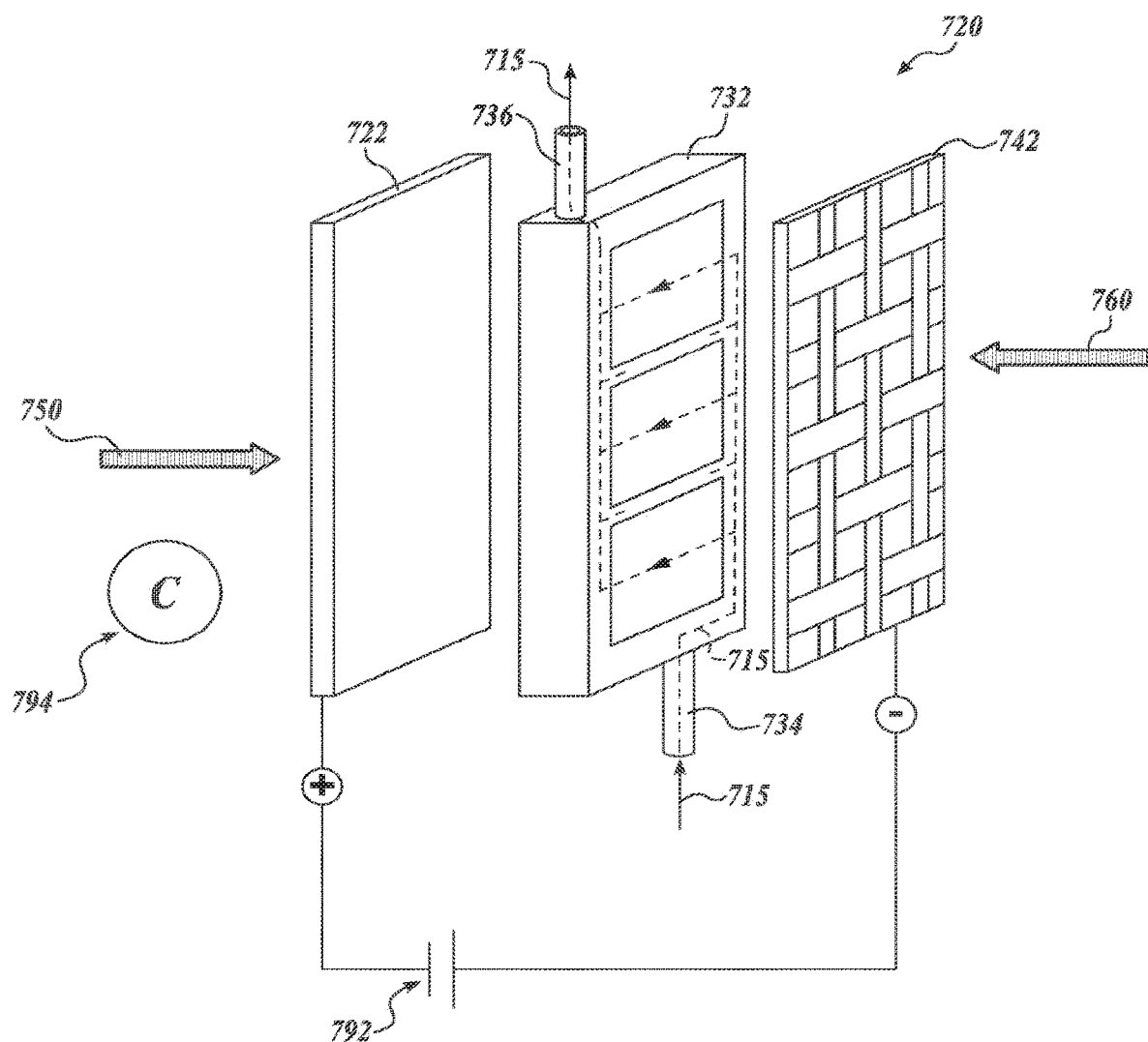
FIG. 5A is an exploded view of a urea treatment unit in accordance with an embodiment of the present technology.

FIG. 5A is an exploded view of a urea treatment unit 720 in accordance with an embodiment of the present technology. The electrochemical reaction that takes place in the urea treatment unit 720 may be described as:

Anode: $CO(NH_2)_2 + 6OH^- \rightarrow CO_2 + N_2 + 5H_2O + 6e^-$

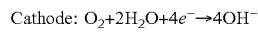
Cathode: $O_2 + 2H_2O + 4e^- \rightarrow 4OH^-$

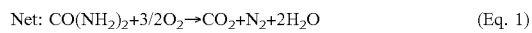
Net: $CO(NH_2)_2 + 3/2 O_2 \rightarrow CO_2 + N_2 + 2H_2O$ (Eq. 1)

In some embodiments, dialysate 715 flows through a spacer 732 from an inlet 734 to an outlet 736. Dialysate 715 carries urea that is to be electrochemically decomposed into $CO_2$ and $N_2$. The spacer 732 may be sandwiched between an anode 722 and a cathode 742, each individually connected to a source of voltage 792 (e.g., a source of DC voltage). In some embodiments the source of voltage 792 provides voltage differential within a range from about 0.6 V to about 0.8 V. In some embodiment of spacer 732, the entire dialysate flow is directed to flow over $TiO_2$ layer.

In some embodiments, the anode 722 is fitted with nanostructures (e.g., $TiO_2$ nanowires). In operation, the anode 722 is illuminated by a source of light that emits light (e.g., UV light) for the electrochemical reaction shown in equation 1. At the anode, photo-excited $TiO_2$ nanostructures provide holes for the oxidation of solution species on the surface, while electrons are collected on underlying conducting oxide (e.g., fluorine doped thin oxide or FTO), and then transported to the cathode electrode to split water into OH. The photo-excitation may be provided by a source of light 750 or by natural light.

In some embodiments, the cathode 742 may be gas permeable (e.g., air permeable or oxygen permeable). In operation, flow of gas 760 that includes oxygen can pass through the cathode 742 toward the dialysate that includes urea.

In some embodiments, the urea treatment unit 720 may be used for preparing a dialysis fluid. For example, water to be treated may be passed between the anode 722 and the cathode 742 to oxidize impurities in the water to be treated, thereby generating the dialysis fluid. Some embodiments of the urea treatment unit 720 are further described with reference to FIGS. 5B-6B below.

Figure 5B:
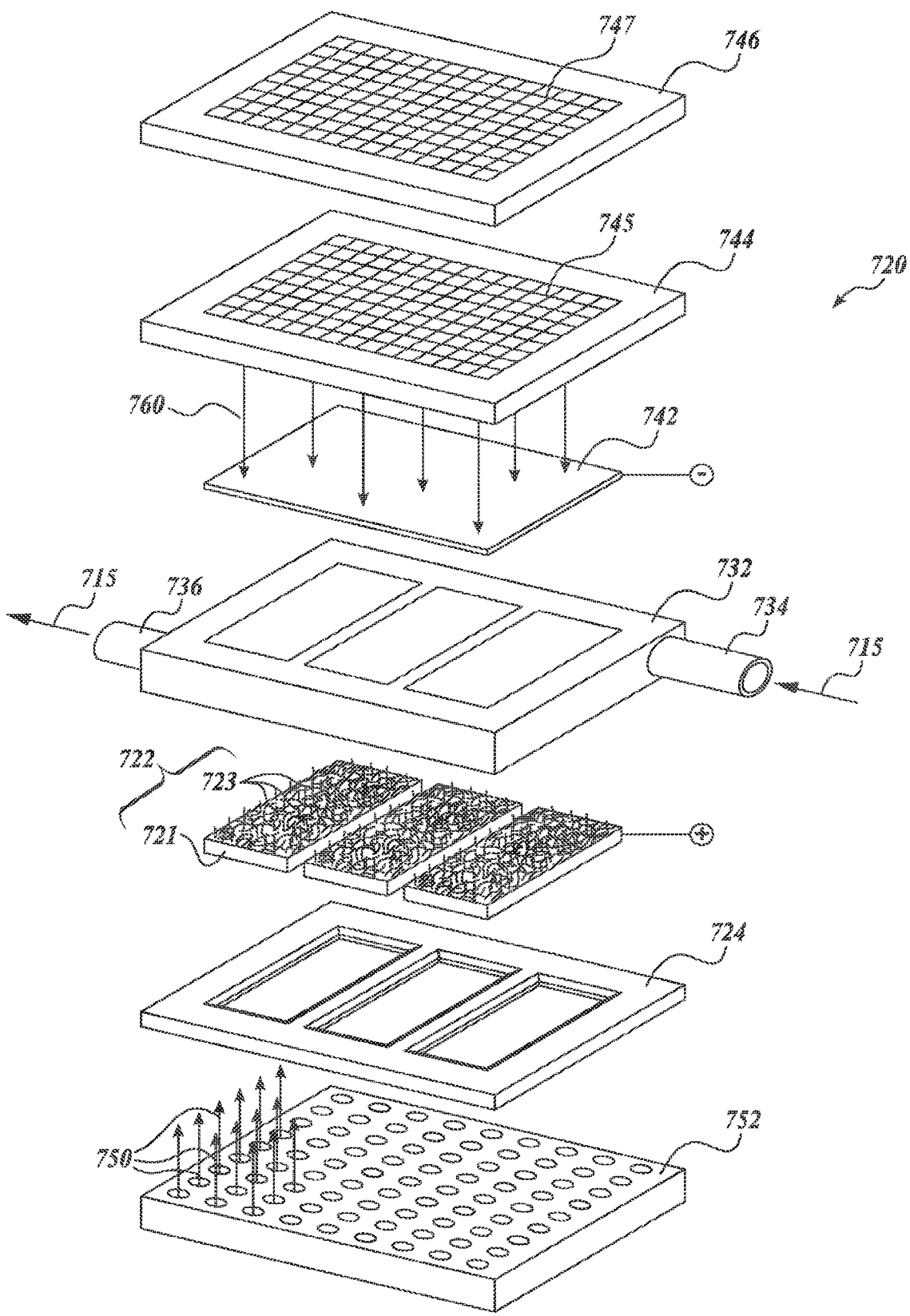
FIG. 5B is an exploded view of a urea treatment unit in accordance with an embodiment of the present technology.

FIG. 5B is an exploded view of a urea treatment unit 720 in accordance with an embodiment of the present technology. In some embodiments, the urea treatment unit 720 includes one or more nanostructured anodes 722 having a substrate 721 that carries nanostructures 723. The nanostructured anode 722 may be held in a substrate holder 724. The light required for the photo-chemical decomposition of the urea may be provided by a light array 752 that includes one or more sources of light (e.g., light emitting diodes (LEDs), lasers, discharge lamps, etc.). The sources of light may be arranged in a 2-dimensional (2D) array. In some embodiments, the LEDs emit light at 365 nm wavelength. In some embodiments, the LEDs emit light at an ultraviolet (UV) or visible light wavelength. In some embodiments, the LEDs generate light with the intensity of less than 4 mW/cm² at the surface of the anode (e.g., at the surface of the substrate 721). In other embodiments, other, higher light intensities may be used, for example light with the intensity of more than mW/cm² at the surface of the anode. In some embodiments, quantum efficiency of incident photons (incident photo-electric efficiency) is about 51%. In some embodiments, the nanostructured anode 722 may operate based on the incoming natural light in conjunction with or without dedicated light array 752.

As explained with reference to FIG. 5A, the cathode may be an air permeable cathode 742 that blocks liquids (e.g., water), but passes gases (e.g., air or oxygen) through. In some embodiments, the cathode 742 is made of conductive cloth. For example the conductive cloth may be a platinum-coated (Pt-coated) cloth or carbon cloth. In some embodiments, the cathode 742 may be a conductive paper-based cathode. The air permeable (air breathable) cathode 742 may be mechanically held in place by spacers 744 and 746 having supporting elements for the cathode 742, for example the spacers having mesh supporting elements 745, 747 (or other gas-permeable structural elements).

With at least some embodiments of the inventive technology, significant performance improvements were observed when compared to the performance of the conventional technology. For example, matching a daily urea production to the 6e– oxidation process for 15 gram (0.25 moles) a day target requires electrical current of 1.7 A over a 24 hour period. With a target 1 mA/cm² photocurrent density on the TiO₂ nanostructured anode, the required total device area becomes about 1700 cm², or 1.82 ft². With such total device area it becomes feasible to deploy a backpack sized device that oxidizes about 15 g of urea per day. The backpack sized device would require about twelve 8000 mAh batteries for 8 hour operation without recharging and proportionally less batteries for shorter operations.

Furthermore, the high conversion efficiency of urea decomposition at low concentrations shows a high selectivity of TiO₂ to oxidize urea vs. generating oxochloro-species that are generally undesirable. Additionally, photocurrent density is more than one order of magnitude higher than that achieved by the prior art without nanostructures or LEDs.

Sample Calculation of Device Performance

For the illustrated embodiment, the operating current of the UV LED was kept at 50 mA. With 6.7% of photons being geometrically incident on the TiO₂ sample, we can obtain the incident LED current to photoelectron current efficiency by $$\eta = \frac{I_{photocurrent}}{6.7\% \times I_{LED}},$$

where $I_{LED}$ and $I_{photocurrent}$ are the current used to drive the LED and the resultant photocurrent, respectively. Since the LED quantum efficiency is 40%, the incident photon to photoelectron efficiency $$\eta' = \frac{\eta}{40\%}.$$

The total amount of photocurrent passing through the circuit is calculated with $Q_{total} = \int I_{photocurrent} dt$. Cumulative photocurrent that was used for urea decomposition can be calculated from urea concentration change, that is $Q_{urea} = 6 \times 96485 \times (C_{start} - C_{end}) \times V$, where 6 is the number of electrons involved in oxidizing a single urea molecule times Faraday's constant, $C_{start}$ and $C_{end}$ are urea concentrations measured before and after the photo-oxidation experiment, and V is 0.3 ml. Selectivity of the photocurrent towards urea decomposition is $$\eta = \frac{Q_{urea}}{Q_{total}}.$$

Urea removal rate is assumed to be constant during the operation. To calculate the required electrode area and operating current, we may assume 15 g of urea needs to be removed daily.

In contrast with the inventive technology, the prior art technology requires much higher operating current. To calculate the incident photon to photoelectron efficiency for the prior art technology as shown in Table 1 below, the solar AM 0.15 spectrum from NREL is used, which the light source in the literature was emulating. For the 100 mW/cm² intensity used in the literature, the total photon flux becomes $3.89 \times 10^{17}$ s⁻¹cm⁻², out of which the photons between 280 nm and 380 nm have the flux of $1.16 \times 10^{16}$ s⁻¹cm⁻². Thus the incident photo to photonelectron efficiency is 0.28%. Even considering only the wavelengths below 380 nm, the efficiency remains only 9.3%. Assuming 40% quantum efficiency of the light source, same as the UV LED used in this study, this would require an operating current of 2000 A that is not practical in clinical, home or portable use.

Some comparisons of the performance of the present technology and the conventional technology is shown in Table 1 below.

TABLE 1

Comparison between the present and conventional technology

| | Incident photon to photoelectron efficiency | Efficiency of photocurrent toward urea decomposition | Typical Steady state photocurrent (mA/cm²) | Typical urea removal rate g/(cm² · hr) | Required electrode area for 15 g urea removal during 24 hrs (cm²) |
|---|---|---|---|---|---|
| Present technology | 51% | 80% | 0.8 | 2.66e−4 | 2,360 (2.5 sqft) |
| Conventional technology | <0.1% | 97% | 0.011 | 4.03e−6 | 155,000 |

Figure 6B:
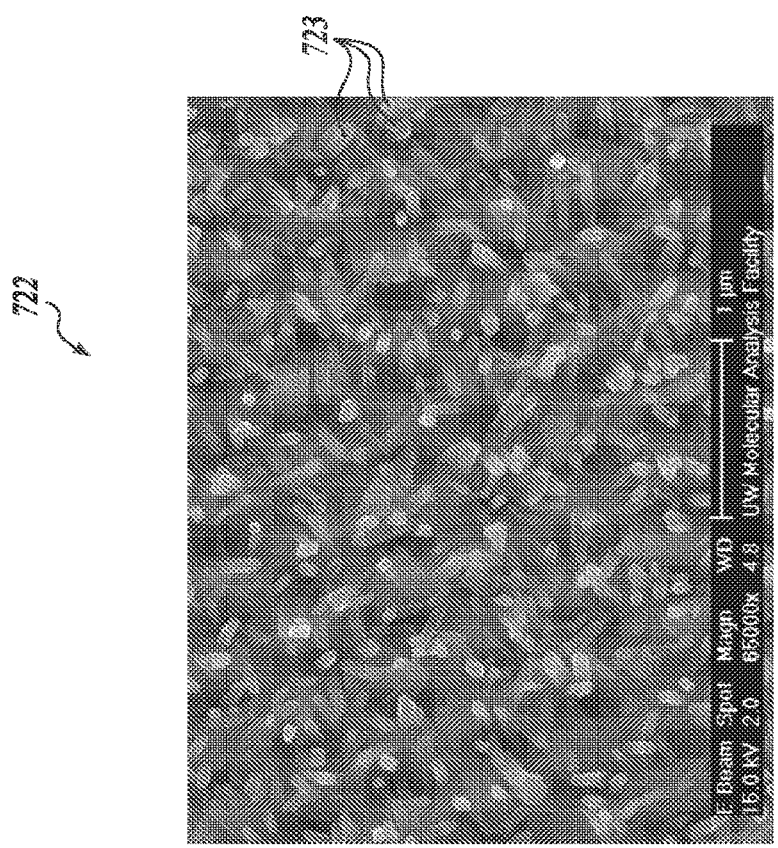
FIGS. 6A and 6B are microscope images of nanostructures in accordance with an embodiment of the present technology.
Figure 6A:
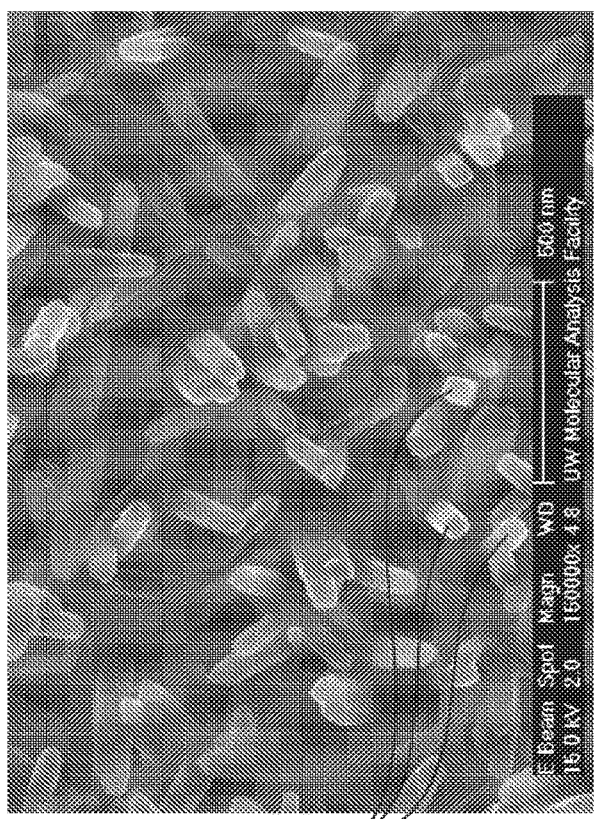

FIGS. 6A and 6B are microscope images of the nanostructures 723 at two different scales in accordance with an embodiment of the present technology. Generally, to improve performance of the $TiO_2$, there is an inherent trade-off of having a sample that is thick enough to absorb all incoming light, but also thin enough to collect electron current without significant amounts of carrier recombination in the bulk of the substrate. In some embodiments, such optimization is obtained by the highly ordered nanoscale structures with high surface area and efficient electrical conduction to electron collection electrode (e.g., a substrate that is an FTO layer). In operation, relatively high density in the vertical direction of the nanostructures 723 allows for the separation of electrons/hole carriers, therefore reducing the inefficient carrier recombination. In some embodiments, the nanostructures 723 are about 500 nm thick.

Figure 7:
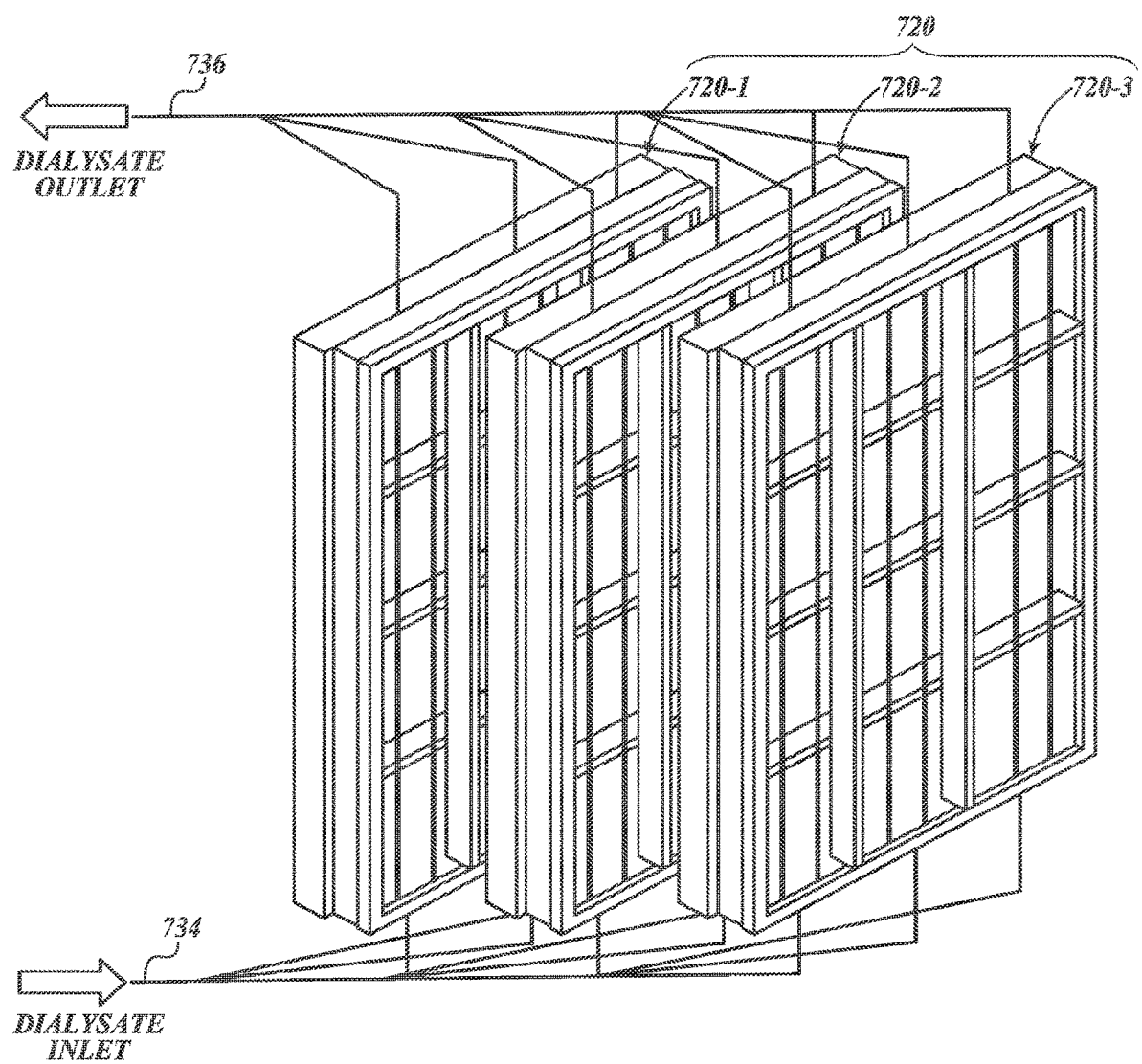
FIG. 7 is a schematic view of a urea treatment unit in accordance with an embodiment of the present technology.

FIG. 7 is a schematic view of a urea treatment unit in accordance with an embodiment of the present technology. The illustrated urea treatment unit 720 includes several cells 720-*i* (also referred to as urea treatment cells, dialysis-fluid regeneration cells, or photo-chemical oxidation cells). In different embodiments, the cells 720-*i* may share the same inlet and/or outlet. The flow of the dialysate through the cell may be arranged as a parallel or serial flow, or as a combination of both. In general, stacking the cells 720-*i* reduces the overall width and height of the system, therefore making the system more compact and portable.

Figure 8:
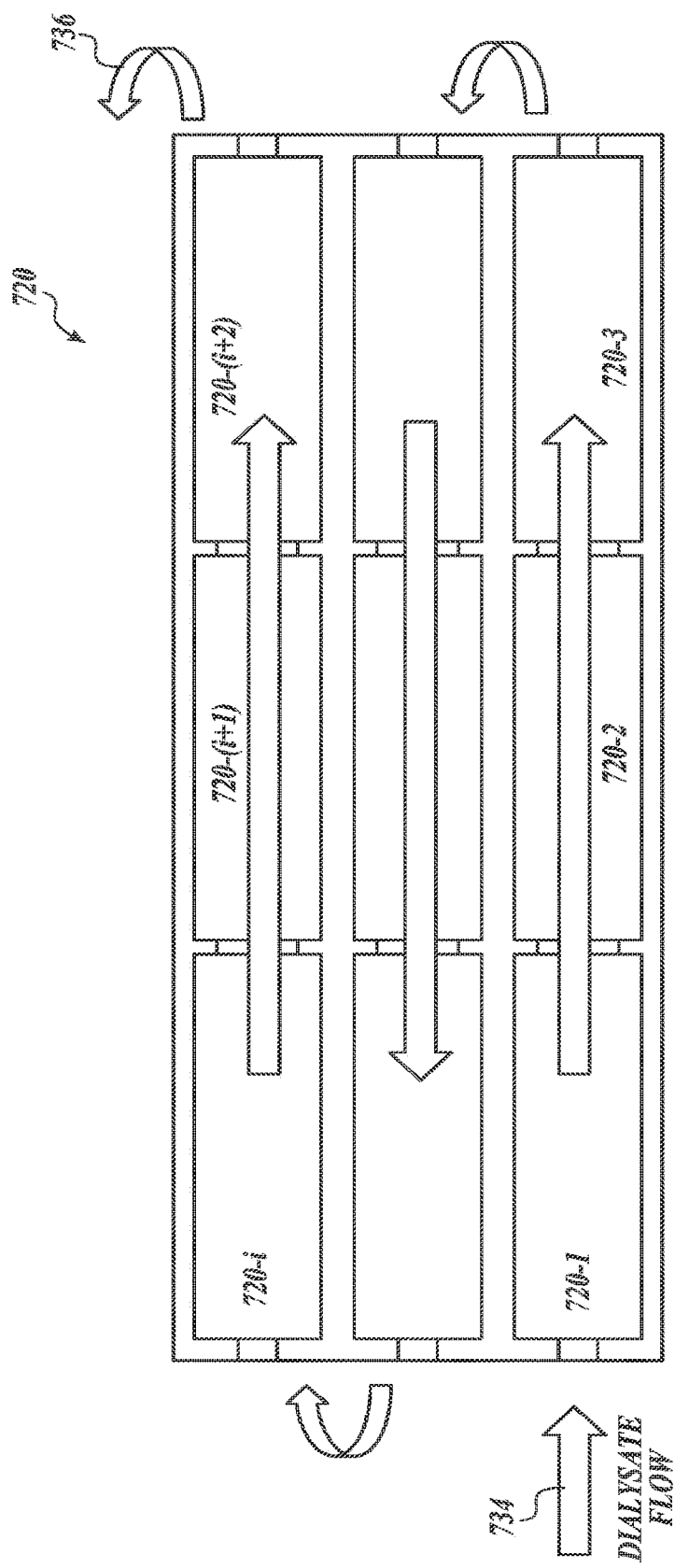
FIG. 8 is flow diagram of a urea treatment unit in accordance with an embodiment of the present technology.

FIG. 8 is flow diagram of a urea treatment unit 720 in accordance with an embodiment of the present technology. The urea treatment unit 720 includes multiple cells 720-*i*. A flow of dialysate enters a cell 720-1, where at least partial decomposition of the urea in the dialysate takes place, and continues towards other cells 720-*i*. Collectively, the electrochemical reaction in the cells 720-*i* convert the urea into the $CO_2$ and $N_2$ as explained with reference to Equation 1 above. In general, arranging the cells 720-*i* may make the system more modular and/or less expensive.

Figure 9:
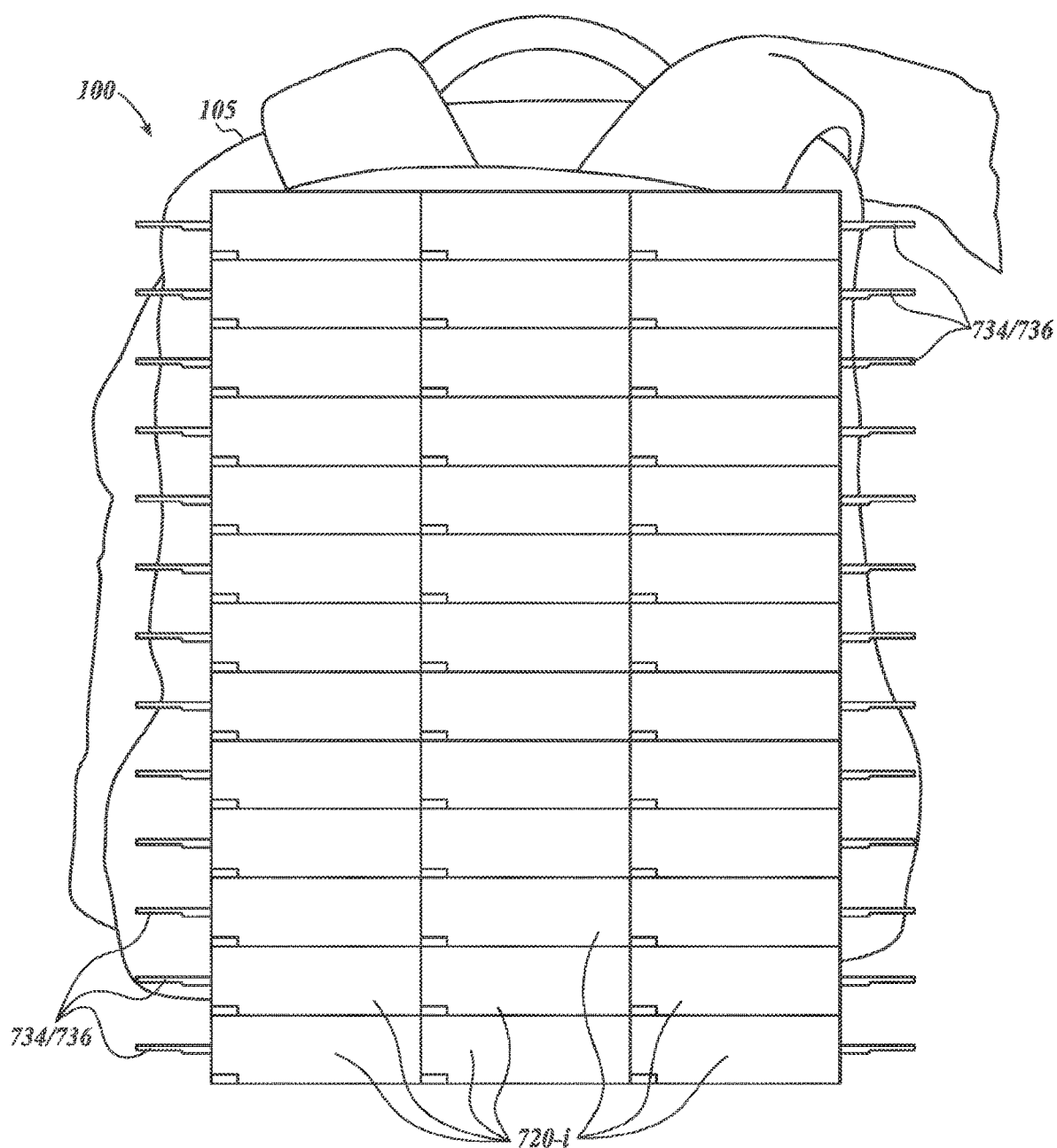
FIG. 9 is a schematic view of a portable urea dialysis system in accordance with an embodiment of the present technology.

FIG. 9 is a schematic view of a portable urea dialysis system 100 in accordance with an embodiment of the present technology. The illustrated system 100 includes multiple cells 720-*i* having multiple dialysate inlets and outlets 734, 736. The flow through the cells 720-*i* may be arranged as shown in FIGS. 7-9. As a result, size of the urea dialysis system 100 may be reduced to such an extent that the system becomes portable, for example, the system may be fitted within a backpack or other carrier 105.

FIGS. 10A-10D are schematic views of portable dialysis systems in accordance with embodiments of the present technology. In some embodiments of the inventive technology, the compactness of the dialysis system may enable wearability or portability of the system. Such wearability/portability of the dialysis system promotes mobility and quality of life of the patient.

Figure 10A:
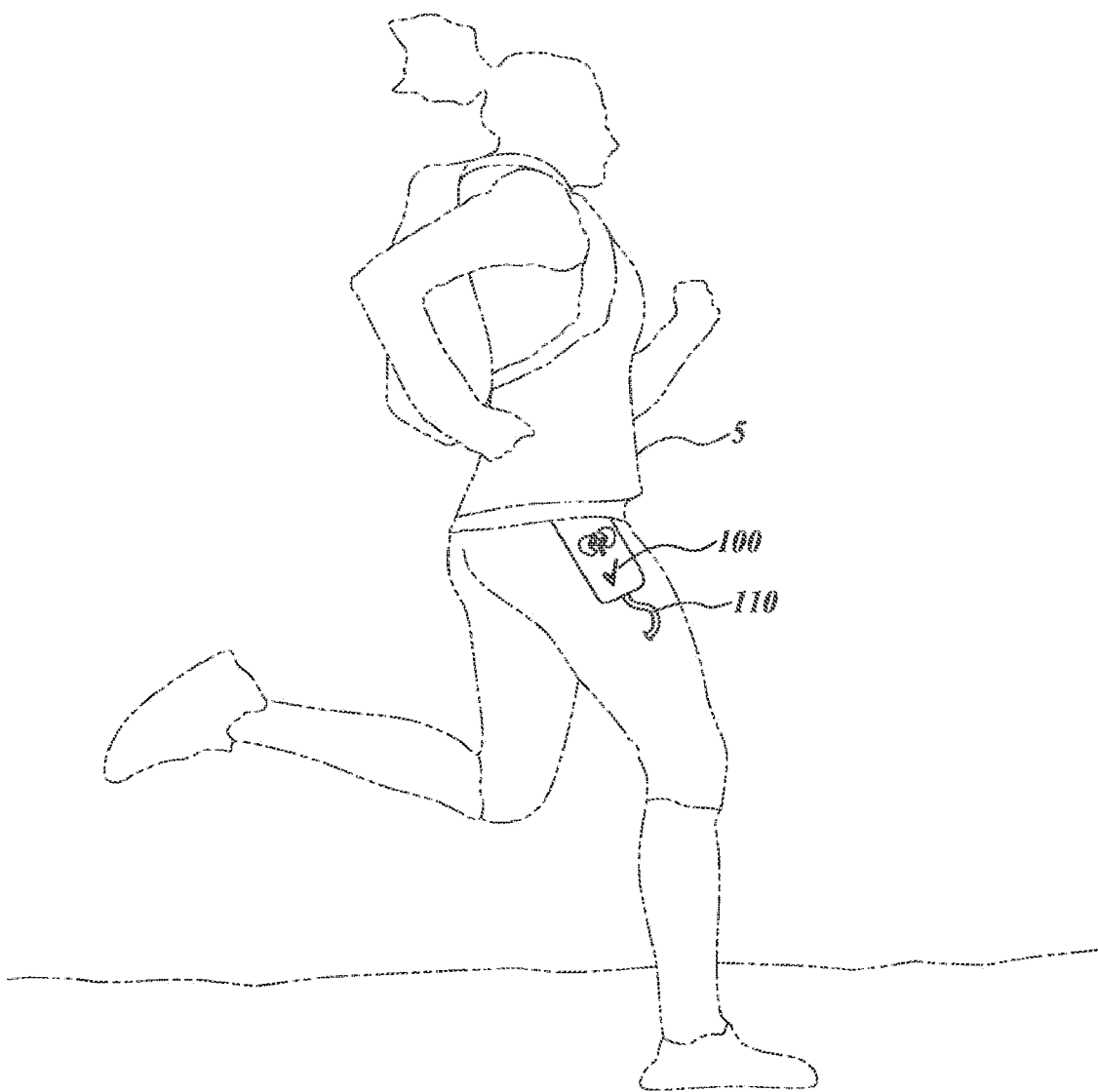
FIGS. 10A-10D are schematic views of portable dialysis systems in accordance with embodiments of the present technology.
Figure 10B:
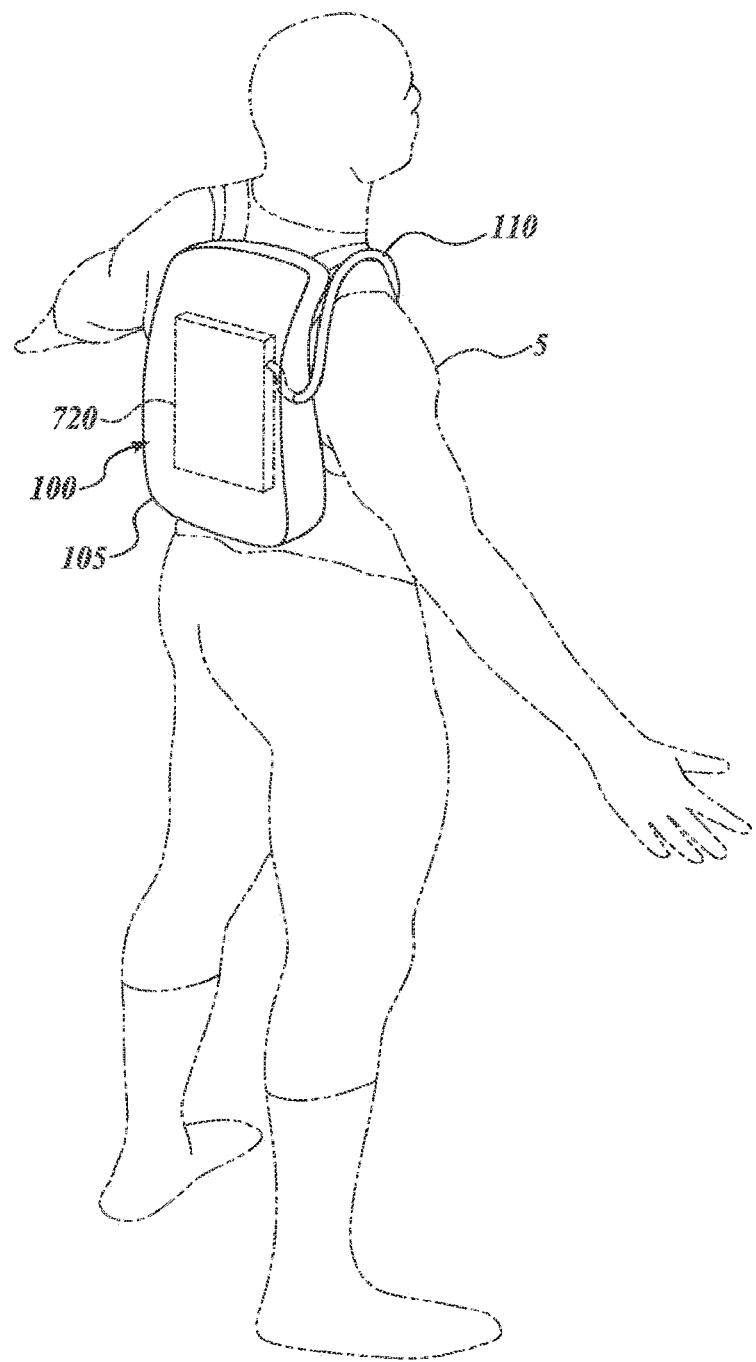
Figure 10C:
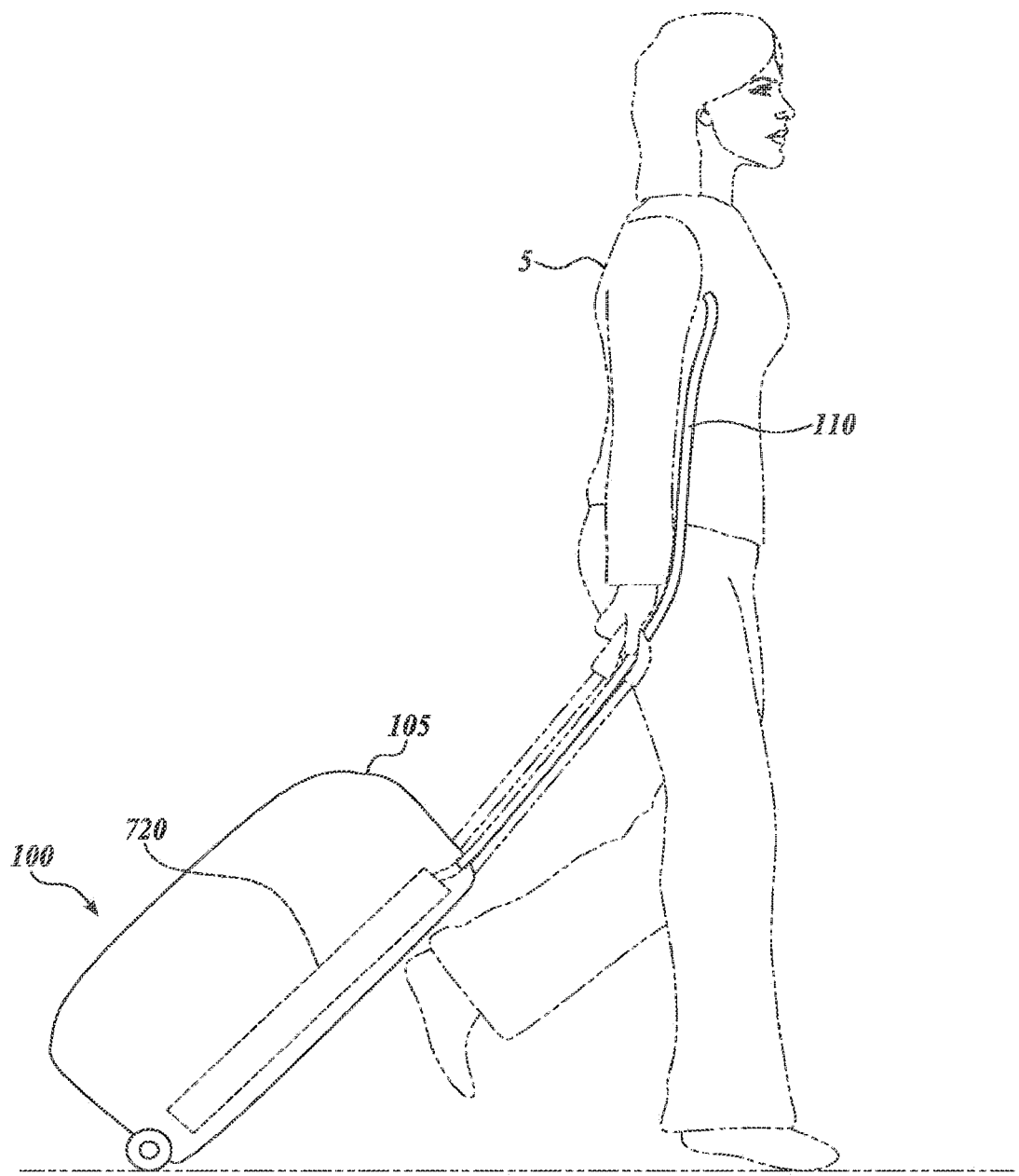
Figure 10D:
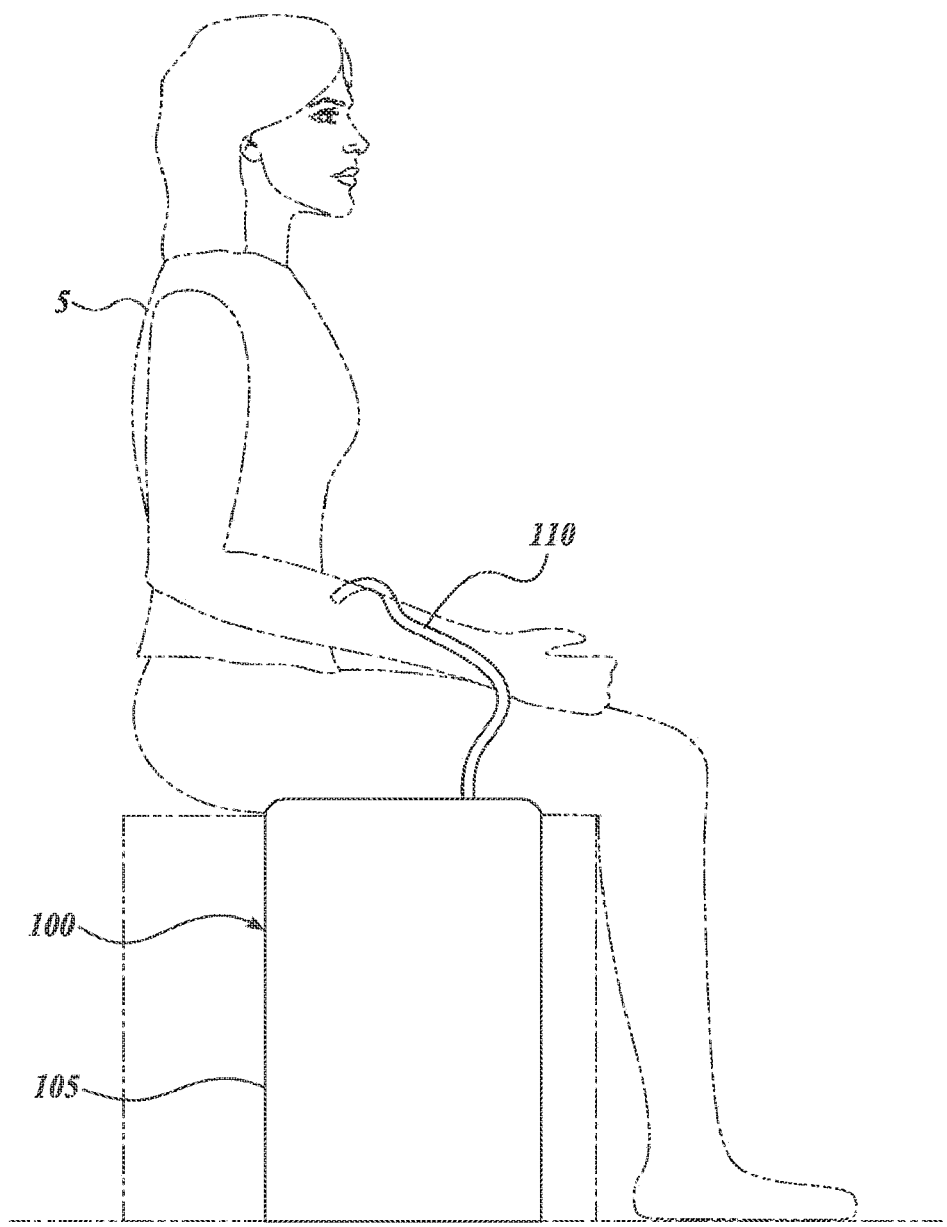

FIG. 10A illustrates a portable dialysis system 100 that is attached to a body of the patient 5. The portable dialysis system 100 is connected to the vascular system of the patient with a tube 110, with other possible embodiments of vascular access locations. FIG. 10B illustrates a portable dialysis system 100 that includes the urea treatment unit 720 that can be fitted within the backpack 105. FIG. 10C illustrates a portable dialysis system 100 that includes the urea treatment unit 720 that can be fitted within a suitcase 105. FIG. 10D illustrates a portable dialysis system 100 that includes the urea treatment unit that can be fitted within a case 105. Other examples of the portable dialysis system 100 are also possible in different embodiments.

Figure 11:
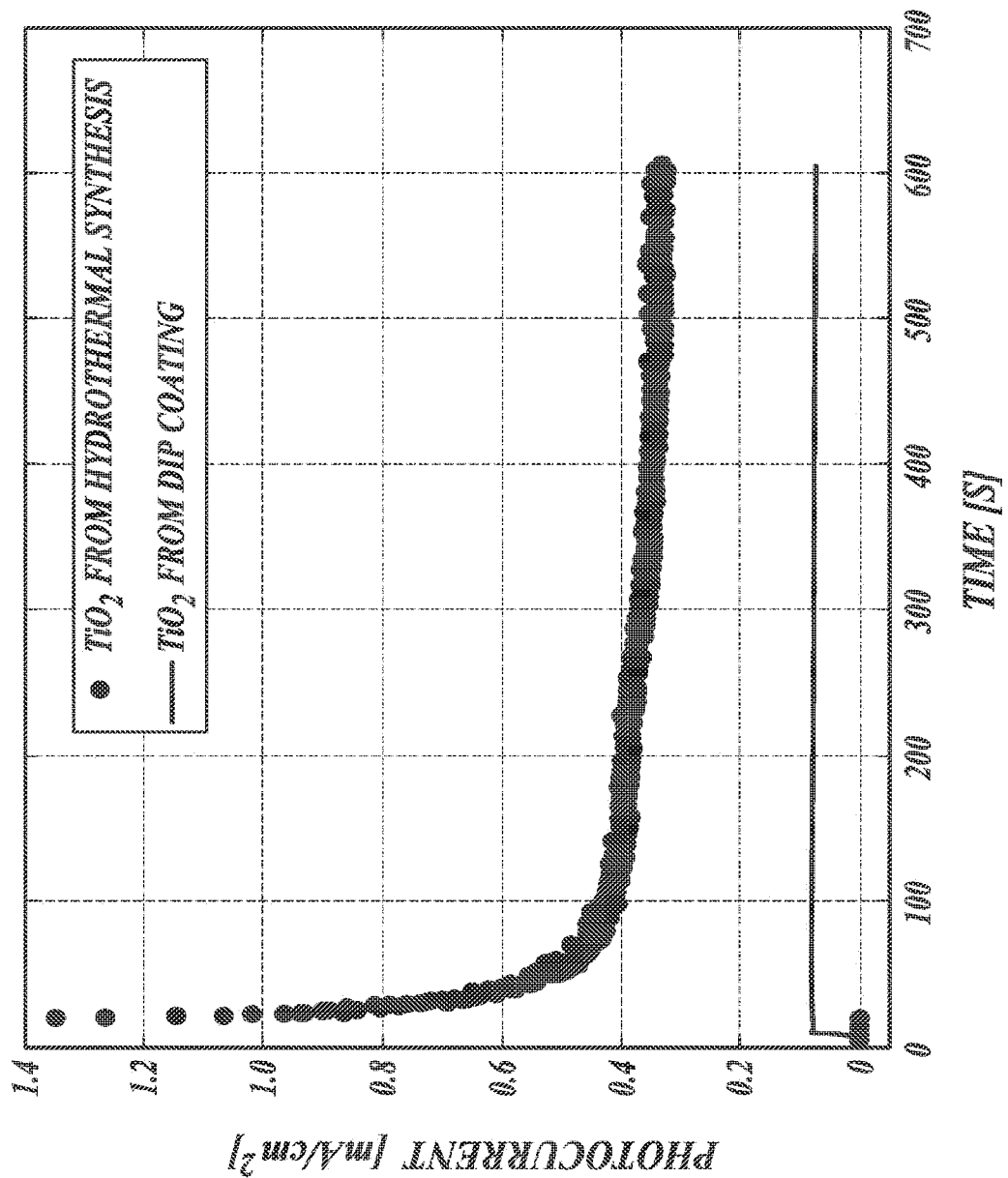
FIG. 11 is a graph of photocurrent in accordance with an embodiment of the present technology.

FIG. 11 is a graph of photocurrent in accordance with an embodiment of the present technology. The horizontal axis of the graph shows time in seconds, and the vertical axis shows the photocurrent in $mA/cm^2$. Data were obtained by illuminating the $TiO_2$ nanostructures that were manufactured by hydrothermal synthesis (upper curve) and dip coating (lower curve). When acquiring data, the LED is turned on (50 mA) at 5 s into the measurements; 0V is applied to $TiO_2$; and static urea/NaCl solution is used. The $TiO_2$ film that was made by hydrothermal synthesis shows high initial current. This initial current is mass-transport limited and has about 8× higher steady state photocurrent than the $TiO_2$ film that was prepared by dip coating. The effective LED intensity on the $TiO_2$/FTO substrate was 4 $mW/cm^2$.

Figure 12:
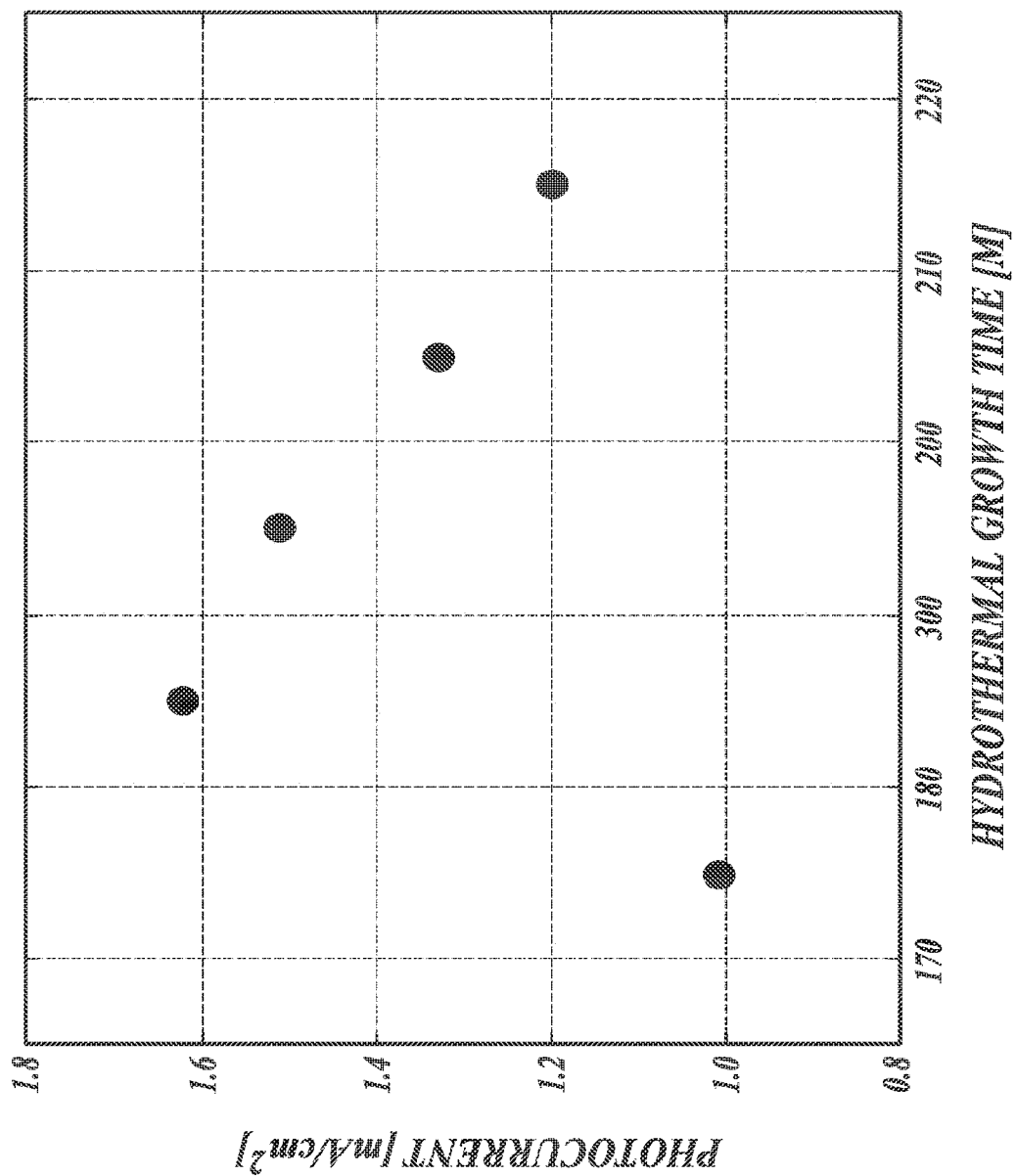
FIG. 12 is a graph of photocurrent as a function of hydrothermal growth time in accordance with an embodiment of the present technology.

FIG. 12 is a graph of photocurrent as a function of hydrothermal growth time in accordance with an embodiment of the present technology. The horizontal axis of the graph shows time in seconds, and the vertical axis shows the photocurrent in $mA/cm^2$. The effective LED intensity on $TiO_2$/FTO substrate was 4 $mW/cm^2$. A steady state photocurrent as a function of hydrothermal growth time shows optimal growth time at about 185 min (corresponding to the maximum photocurrent).

Figure 13:
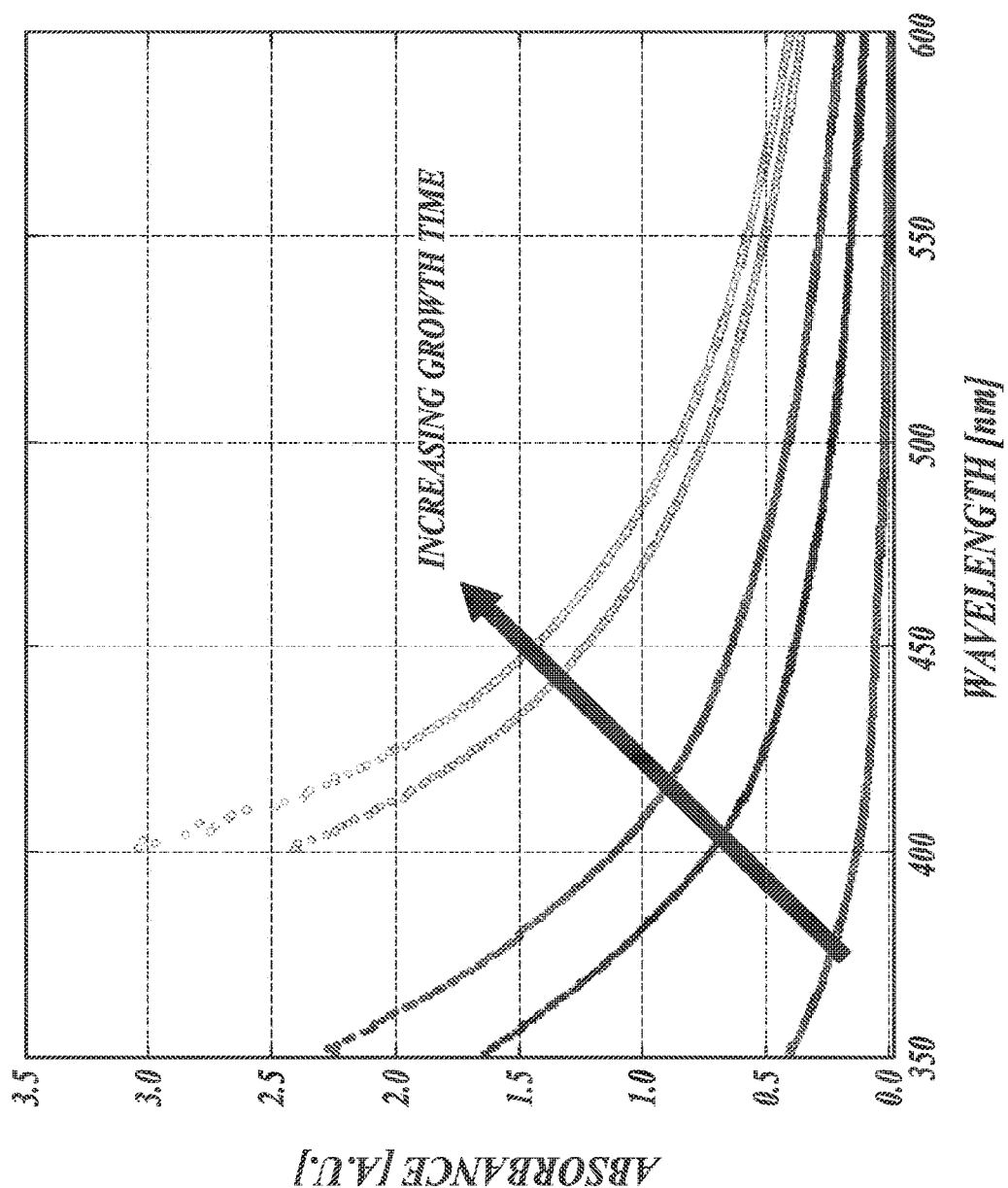
FIG. 13 is a graph of absorbance as a function of wavelength in accordance with an embodiment of the present technology.

FIG. 13 is a graph of absorbance as a function of wavelength in accordance with an embodiment of the present technology. The horizontal axis of the graph shows wavelength of the incoming light in nanometers, and the vertical axis shows the absorbance in atomic units. Ultraviolet light absorbance spectra generally increases with the hydrothermal growth time (the time steps being the same as those shown sequentially in FIG. 12 above).

Figure 14:
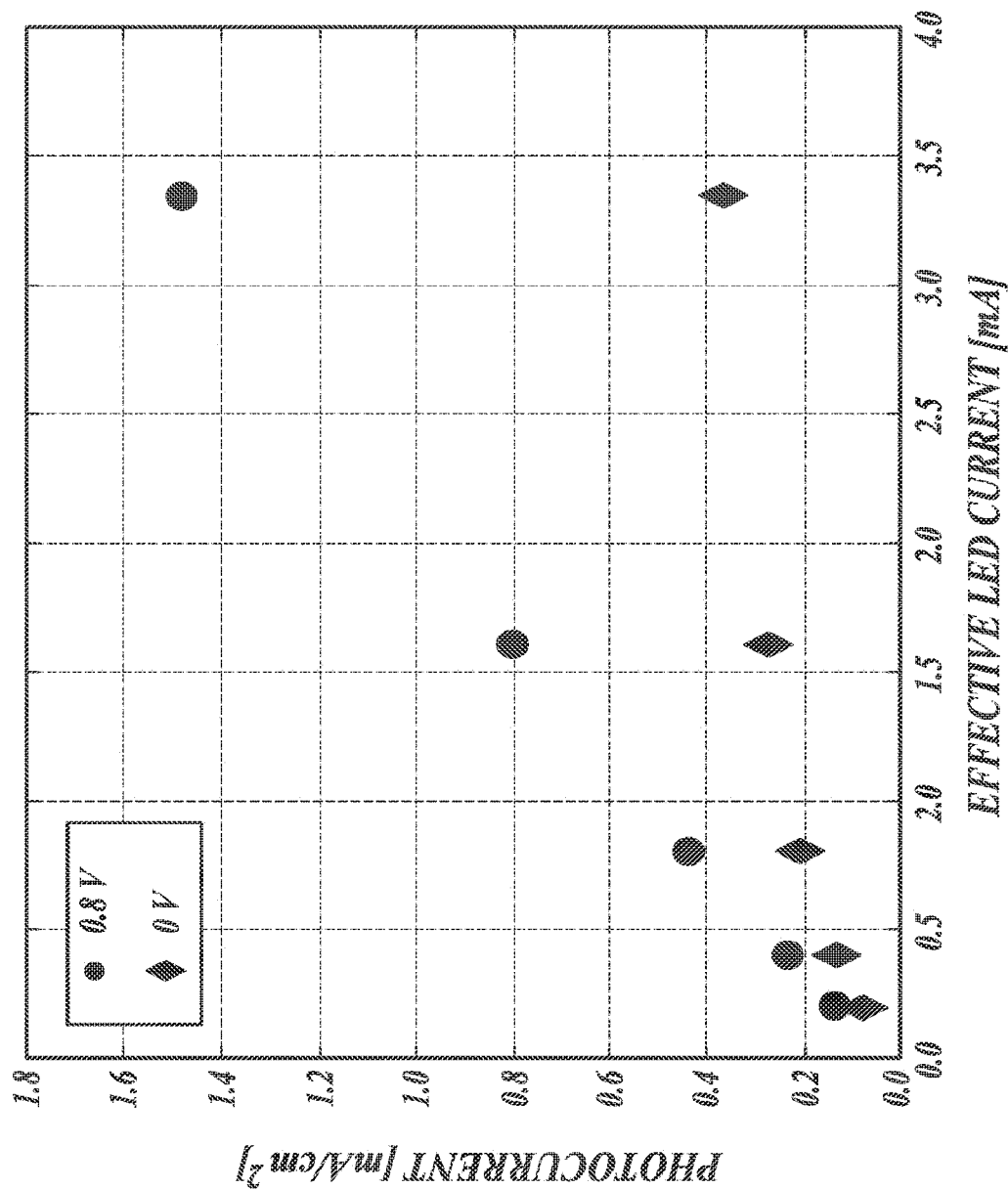
FIG. 14 is a graph of photocurrent as a function of effective LED current in accordance with an embodiment of the present technology.

FIG. 14 is a graph of photocurrent as a function of effective LED current (light intensity) in accordance with an embodiment of the present technology. The horizontal axis of the graph shows effective LED current in mA, and the vertical axis shows the photocurrent in $mA/cm^2$. The round symbols correspond to the applied cathode-to-anode voltage potential of 0.8 V, and the diamond symbols correspond to the case with no cathode-to-anode voltage. Thus, the graph shows a steady state photocurrent increase significantly with +0.8V applied bias to the $TiO_2$ anode. The increase is due to separating electron hole pairs in $TiO_2$, pushing holes to reaction surface and drawing electrons into cathode circuit. The effective LED current is the portion of the LED current that is responsible for the photons incident on the substrate being tested (the LED having 40% quantum efficiency). Due to the device geometry, only 6.7% of emitted photons were incident on the $TiO_2$ surface (i.e., on the $TiO_2$ substrate surface).

Figure 15:
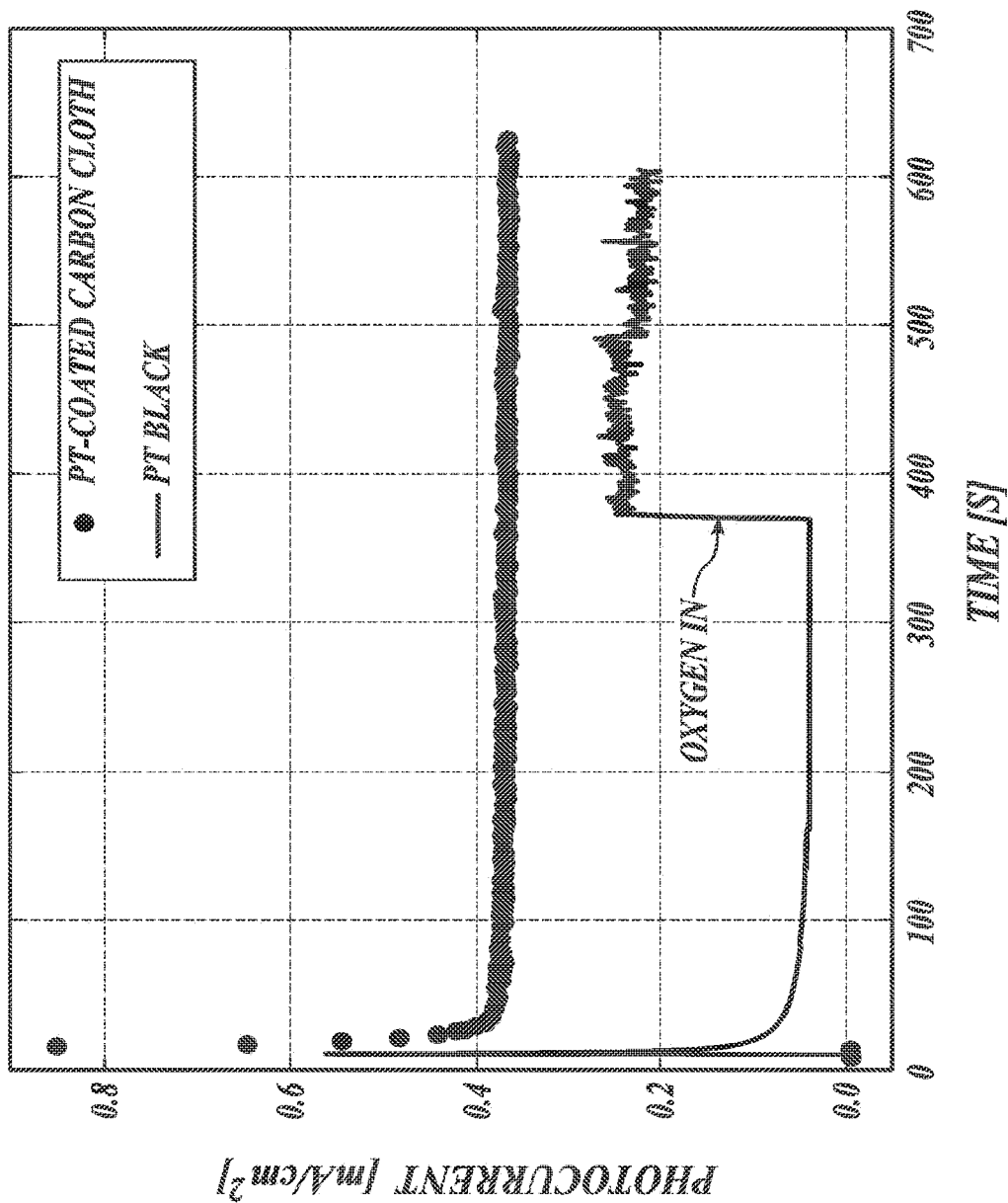
FIG. 15 is a performance comparison between a Pt-coated and a Pt-black cathode in accordance with an embodiment of the present technology.

FIG. 15 is a performance comparison between a Pt-coated and a Pt-black cathode in accordance with an embodiment of the present technology. The horizontal axis of the graph shows time in seconds, and the vertical axis shows the photocurrent in $mA/cm^2$. The LED light was turned on at about 5 s with 0 V applied to anode, and with a static urea solution. The effective LED intensity on $TiO_2$/FTO substrate was 4 $mW/cm^2$. For the Pt-black electrode, air bubbles (2 mL/min) were introduced at 370 s. This event causes the sudden increase in the photocurrent for the Pt-black cathode. Nevertheless, the Pt-coated cathode consistently outperformed the Pt-black cathode in terms of the photocurrent.

Figure 16:
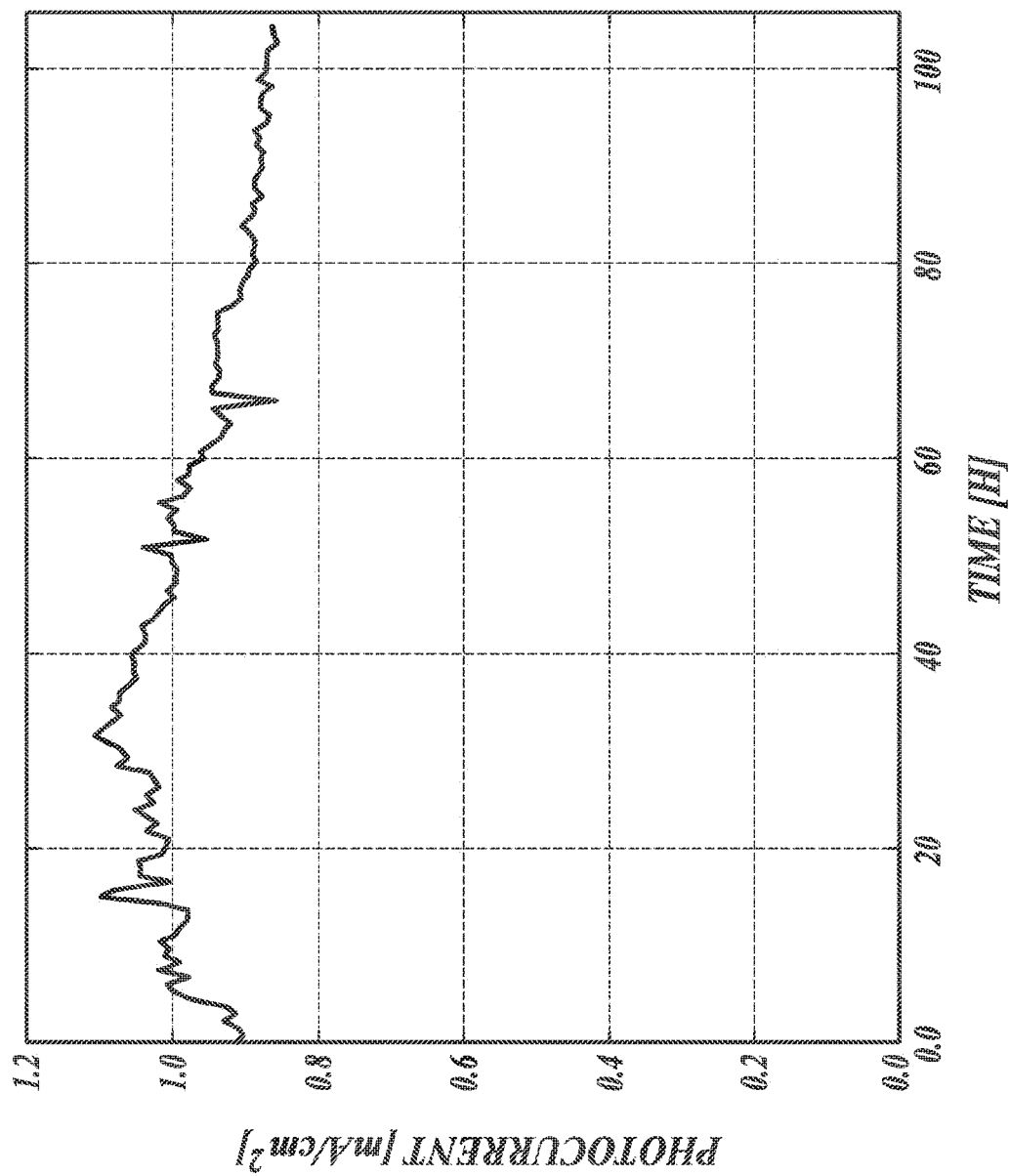
FIG. 16 is a graph of photocurrent as a function of time in accordance with an embodiment of the present technology.

FIG. 16 is a graph of photocurrent as a function of time in accordance with an embodiment of the present technology. The effective LED intensity on $TiO_2$/FTO substrate was 4 $mW/cm^2$. The results demonstrate almost continuous operation of a prototype device running for over 100 h in a circulated (0.3 ml/min) solution of 10 mM urea and 0.15 M NaCl.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like). The term "about" means +/−5% of the stated value.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. A dialysis fluid regeneration system, comprising:
a nanostructured photo-electrochemical anode;
a source of light configured to illuminate the photo-electrochemical anode; and
a cathode that is permeable to oxygen provided to a dialysis fluid and non-permeable to a liquid of the dialysis fluid,
wherein the photo-electrochemical anode is configured to be in contact with the dialysis fluid, and configured to regenerate the dialysis fluid by converting urea in the dialysis fluid into $CO_2$, $N_2$ and $H_2O$ through a photo-electrochemical reaction.

2. The dialysis fluid regeneration system of claim 1, wherein the dialysis fluid is a dialysate.

3. The dialysis fluid regeneration system of claim 1, wherein the dialysis fluid regeneration system is a kidney dialysis system.

4. The dialysis fluid regeneration system of claim 3, wherein the dialysis fluid regeneration system is a hemofiltration system, or a hemodialysis system, or a hemodiafiltration system.

5. The dialysis fluid regeneration system of claim 1, further comprising a source of electrical voltage operationally coupled to the photo-electrochemical anode and the cathode.

6. The dialysis fluid regeneration system of claim 5, wherein the source of electrical voltage is portable.

7. The dialysis fluid regeneration system of claim 1, wherein the dialysis fluid regeneration system is portable or wearable.

8. The dialysis fluid regeneration system of claim 1, wherein the dialysis fluid regeneration system is stationary.

9. The dialysis fluid regeneration system of claim 1, wherein the photo-electrochemical anode, the source of light, and the cathode that is permeable to the oxygen and nonpermeable to the liquid of the dialysis fluid are parts of one dialysis-fluid regeneration cell, and wherein the dialysis fluid regeneration system comprises a plurality of additional dialysis-fluid regeneration cells.

10. The dialysis fluid regeneration system of claim 1, wherein the cathode is an air-breathable cathode.

11. The dialysis fluid regeneration system of claim 10, wherein the cathode is a conductive cloth-based cathode or a conductive paper-based cathode.

12. The dialysis fluid regeneration system of claim 11, wherein the cloth-based cathode comprises a platinum-coated cloth.

13. The dialysis fluid regeneration system of claim 11, wherein the cathode is configured to electrochemically split water.

14. The dialysis fluid regeneration system of claim 1, wherein nanostructures of the photo-electrochemical anode are configured to generate photo-electrons or holes when exposed to light emitted by the source of light.

15. The dialysis fluid regeneration system of claim 1, wherein the source of light comprises an array of light emitting diodes (LEDs).

16. The dialysis fluid regeneration system of claim 15, wherein the LEDs are arranged in a two-dimensional (2D) array.

17. The dialysis fluid regeneration system of claim 15, wherein the LEDs generate an irradiance of less than 4 $mW/cm^2$ at a surface of the photo-electrochemical anode.

18. The dialysis fluid regeneration system of claim 15, wherein the LEDs emit light at 365 nm wavelength.

19. The dialysis fluid regeneration system of claim 1, wherein the source of light comprises a source of UV.

20. The dialysis fluid regeneration system of claim 1, wherein the source of light comprises a source of visible light.

21. The dialysis fluid regeneration system of claim 14, wherein an incident photon to photoelectron efficiency is about 51%.

22. The dialysis fluid regeneration system of claim 1, wherein the nanostructured photo-electrochemical anode comprises $TiO_2$ nanowires.

23. The dialysis fluid regeneration system of claim 22, wherein individual nanowires have a thickness of about 500 nm.

24. The dialysis fluid regeneration system of claim 22, wherein the $TiO_2$ nanowires are prepared hydrothermally.

25. The dialysis fluid regeneration system of claim 22, wherein the nanowires are disposed on a substrate, and wherein the individual nanowires are individually electrically coupled to the substrate that carries the nanowires.

26. The dialysis fluid regeneration system of claim 1, further comprising a dialysate solution having a concentration of urea of 10 mM or less.

27. The dialysis fluid regeneration system of claim 1, further comprising a radical scavenger configured to remove oxidative byproducts, radical byproducts, and chlorine.

28. The dialysis fluid regeneration system of claim 1, further comprising a membrane, wherein the membrane is a reverse osmosis (RO) membrane.

* * * * *